United States Patent [19]
Occelli et al.

[11] Patent Number: 5,786,350
[45] Date of Patent: Jul. 28, 1998

[54] 36-DERIVATIVES OF RIFAMYCINS AND THEIR USE AS ANTIMICROBIAL AGENTS

[75] Inventors: Emilio Occelli, Parabiago; Sergio Lociuro, Milan; Romeo Ciabatti, Novate Milanese, all of Italy; Maurizio Denaro, Cincinnati, Ohio

[73] Assignee: Gruppo Lepetit S.p.A., Milan, Italy

[21] Appl. No.: 792,035

[22] PCT Filed: May 5, 1994

[86] PCT No.: PCT/EP94/01428

§ 371 Date: Jan. 22, 1996

§ 102(e) Date: Jan. 22, 1996

[87] PCT Pub. No.: WO94/28002

PCT Pub. Date: Dec. 8, 1994

Related U.S. Application Data

[63] Continuation of Ser. No. 535,233, Jan. 22, 1996, abandoned.

[30] Foreign Application Priority Data

| | | |
|---|---|---|
| May 24, 1993 | [EP] | European Pat. Off. ............. 93108337 |
| Jun. 29, 1993 | [EP] | European Pat. Off. ............. 93110315 |

[51] Int. Cl.$^6$ ...................... A61D 31/345; C07D 491/08
[52] U.S. Cl. ................ 514/183; 540/457; 540/458; 546/300
[58] Field of Search .................. 540/487, 458; 514/183; 546/300

[56] References Cited

PUBLICATIONS

Helvetica Chimica Acta vol. 56, No. 7, 1973 pp. 2323–2347 Kump et al.

Journal of Antibiotics vol. 40, No. 12, 1987 (Torro) pp. 1733–1739 Wehrli et al.

*Primary Examiner*—Robert T. Bond
*Attorney, Agent, or Firm*—Ruth E. Homan

[57] ABSTRACT

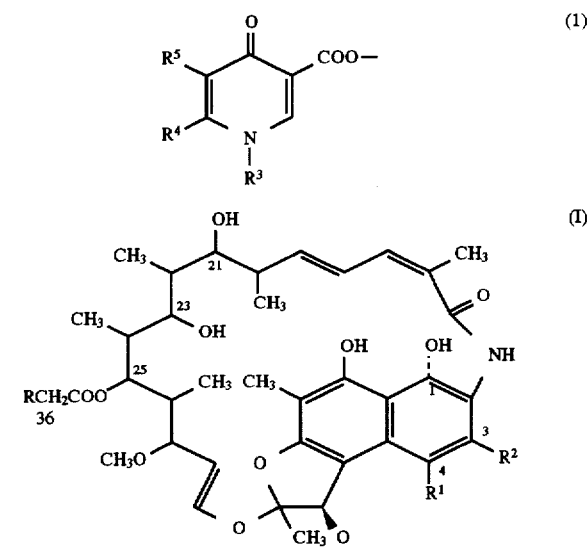

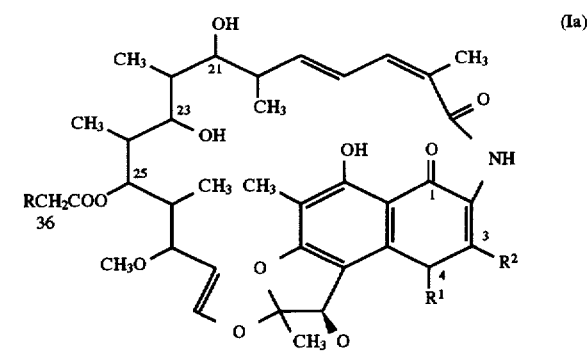

Rifamycin antibiotic derivatives of formulae (I) and (Ia) bearing at the position 36 a substituent selected from ($C_1$–$C_8$)alkyl, halo, hydroxy, ($C_1$–$C_4$)acyloxy, ($C_{1-C4}$) alkoxy, ($C_1$–$C_4$)alkylthio, ($C_1$–$C_4$)alkylamino, di($C_{1-C4}$) alkylamino and substituted 4-oxo-3-pyridinyl carbonyloxy of formula (1) obtained by reacting rifamycin with suitably substituted malonic acid. The compounds of the invention are antimicrobial agents mainly active against gram positive bacteria and fastidious gram negative bacteria showing the considerable antimicrobial activity against the rifamypicin resistant microbial strains.

26 Claims, No Drawings

36-DERIVATIVES OF RIFAMYCINS AND THEIR USE AS ANTIMICROBIAL AGENTS

CROSS-REFERENCE TO RELATED APPLICATION

This is a continuation, of application Ser No. 08/535,233, filed Jan. 22, 1996, abandoned, which is herein incorporated by reference.

This invention relates to novel rifamycin antibiotic derivatives of general formula I:

[Structure I shown: rifamycin derivative with OH, CH₃, RCH₂COO at position 36, etc.]

and to the oxidated derivatives thereof of formula Ia:

[Structure Ia shown: oxidated rifamycin derivative]

wherein:

R represents, halo, hydroxy, thio, $(C_1-C_4)$alkoxy, $(C_1-C_4)$alkylthio, $(C_1-C_4)$acyloxy, $(C_1-C_4)$alkylamino, di$(C_1-C_4)$alkylamino or a group of formula:

[Structure shown: pyridinone with R³, R⁴, R⁵, COO— substituents]

wherein:

$R^3$ represents $(C_1-C_4)$alkyl or $(C_3-C_6)$cycloalkyl;

$R^4$ represents a group of formula

[Structure: R⁶–N–R⁷]

wherein:

$R^6$ and $R^7$ independently represent hydrogen or $(C_1-C_4)$alkyl or $R^6$ and $R^7$ together with the adjacent nitrogen atom form a five or six membered heterocyclic ring, optionally containing one further heteroatom selected from oxygen, nitrogen and sulfur, wherein one of the carbon or nitrogen atoms of the ring is optionally substituted by a $(C_1-C_4)$alkyl moiety;

$R^5$ is hydrogen or halo;

or $R^4$ together with $R^5$ form a bifunctional alkylenic chain, optionally containing 1 or 2 nitrogen atoms, of the following formula:

[Three structures shown with R⁸, R⁹, CH, N substituents]

wherein:

$R^8$ represents hydrogen or halogen;

$R^9$ represents $(C_1-C_4)$alkyl, or a six membered heterocycle ring containing one or two nitrogen atoms, wherein the carbon and nitrogen atoms of the ring are optionally substituted with one or two $(C_1-C_4)$alkyl moieties;

$R^1$ is hydroxy in formula I or oxygen formula Ia;

$R^2$ represents hydrogen, a five or six membered heterocyclic ring containing one or two heteroatoms selected from oxygen, nitrogen and sulfur, wherein one of the carbon or nitrogen atoms of the ring is optionally substituted by a $(C_1-C_4)$alkyl moiety, or a group of formula $$-CH=N-R^{10}$$

wherein $R^{10}$ represents a six membered heterocycle ring containing one or two nitrogen atoms, wherein one of the carbon or nitrogen atoms of the ring is optionally substituted by $(C_1-C_4)$-alkyl or $(C_5-C_6)$cycloalkyl;

or $R^1$ and $R^2$ taken together form a group of formula =N—(CHR¹¹)—X—, —NH—(CHR¹¹)—X—, or —N=(CR¹¹)—X—, wherein:

X represents a sulfur atom or a —NH—group and $R^{11}$ represents hydrogen, $(C_1-C_4)$alkyl, $(C_1-C_4)$alkylamino or di$(C_1-C_4)$alkylamino;

and the pharmaceutically acceptale base addition salts thereof.

in-the present description, the terms used above in defining the meanings of the substituents $R^1$ to $R^{14}$ are intended to have the meanings commonly assigned to them in the art. Accordingly:

$(C_1-C_4)$alkyl represent a linear or branched hydrocarbon moiety containing carbon atoms respectively, such as:
—CH₃,
—CH₂—CH₃,
—CH₂—CH₂—CH₃,
—CH—(CH₃)₂,
—CH₂—CH₂—CH₂—CH₃,
—CH(CH₃)—CH₂—CH₃,
—C(CH₃)₂—CH₂—CH₃,
—CH₂—CH(CH₃)—₃,
—C—(CH₃)₃.

halo represents fluoro, chloro, bromo or ioda;

$(C_1-C_4)$ alkoxy represents a linear or branched ether moiety containing 1, 2, 3 or 4 carbon, such as:
—O—CH₃,
—O—CH₂—CH₃,
—O—CH₂—CH₂—CH₃,
—O—CH—(CH₃)₂,
—O—CH₂—CH₂—CH₂—CH₃,

—O—CH(CH$_3$)—CH$_2$—CH$_3$,
—O—CH$_2$—CH(CH$_3$)—$_3$,
—O—C—(CH$_3$)$_3$.

(C$_1$-C$_4$)acyloxy represents a carboxylic moiety containing 1 to 4 carbon atoms, such as:
—O—CO—H
—O—CO—CH$_3$,
—O—CO—CH$_2$—CH$_3$,
—O—CO—CH$_2$—CH$_2$—CH$_3$,
—O—CO—CH —(CH$_3$)$_2$;

(C$_1$-C$_4$)alkylthio represents a linear or branched thioether moiety with 1 to 4 carbon atoms, such as:
—S—CH$_3$,
—S—CH$_2$—CH$_3$,
—S—CH$_2$—CH$_2$—CH$_3$,
—S—CH—(CH$_3$)$_2$,
—S—CH$_2$—CH$_2$—CH$_2$—CH$_3$,
—S—CH(CH$_3$)—CH$_2$—CH$_3$,
—S—CH$_2$—CH(CH$_3$)—$_3$,
—S—C—(CH$_3$)$_3$.

(C$_1$-C$_4$)alkylamino represents an amino moiety substituted with a linear or branched alkyl containing 1 to 4 carbon atoms, such as:
—NH—CH$_3$,
—NH—CH$_2$—CH$_3$,
—NH—CH$_2$—CH$_2$—CH$_3$,
—NH—CH—(CH$_3$)$_2$,
—NH—CH$_2$—CH$_2$—CH$_2$—CH$_3$,
—NH—CH(CH$_3$)—CH$_2$—CH$_3$,
—NH—CH$_2$—CH(CH$_3$)—$_3$,
—NH—C—(CH$_3$)$_3$.

(C$_1$-C$_4$) dialkylamino represents an amino moiety substituted with two linear or branched alkyl moieties containing 1 to 4 carbon atoms such as:
—N—(CH$_3$)$_2$,
—N(CH$_3$)—CH$_2$—CH$_3$,
—N(CH$_2$—CH$_3$)$_2$,
—N(CH$_3$)—CH$_2$—CH$_2$—CH$_3$,
—N(CH$_2$—CH$_3$)—CH$_2$—CH$_2$—CH$_3$,
—N(CH$_2$—CH$_2$—CH$_3$)$_2$,
—N(CH$_3$)—CH—(CH$_3$)$_2$,
—N(CH$_2$—CH$_3$)—CH—(CH$_3$)$_2$,
—N(CH$_3$)—CH$_2$—CH$_2$—CH$_2$—CH$_3$,
—N(CH$_2$—CH$_3$)—CH$_2$—CH$_2$—CH$_2$—CH$_3$,
—N(CH$_2$—CH$_2$—CH$_3$)—CH$_2$—CH$_2$—CH$_2$—CH$_3$,
—N(CH$_2$—CH$_2$—CH$_2$—CH$_3$)$_2$,
—N(CH$_2$—CH$_2$—CH$_2$—$_3$)—CH—(CH$_3$)$_2$.

(C$_3$-C$_6$)cycloalkyl represent a cyclic hydrocarbon moiety containing from $_3$ to 6 carbon atoms such as:
cyclopropyl,
cyclobutyl,
cyclopentyl,
cyclohexyl.

A five or six membered heterocyclic ring containing one or two heteroatoms selected from oxygen, nitrogen and sulfur (according to the definition of substituents R$^6$ and R$^7$ or R$^9$) is an heterocycle ring such as:

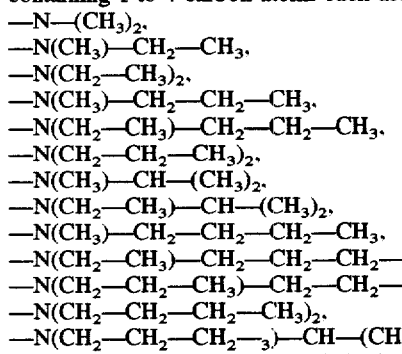

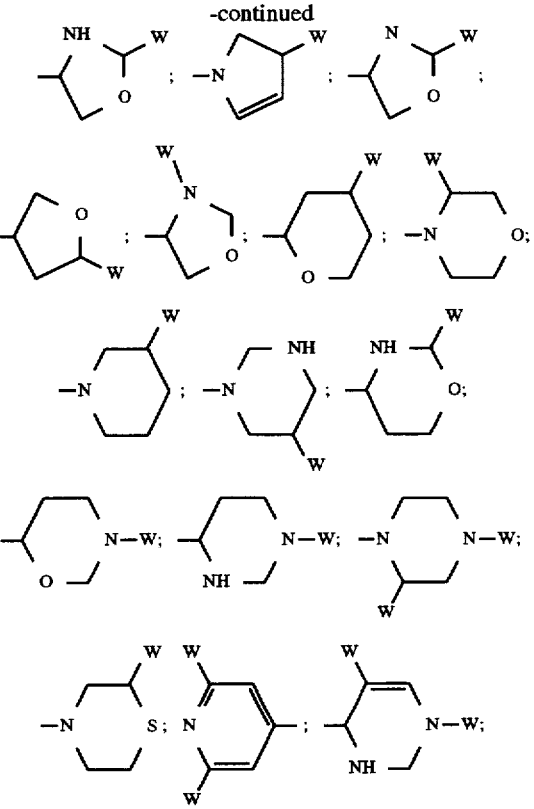

wherein W represents hydrogen or the various possible substituents of the 5 or 6 membered heterocycle ring, according to the definitions set out above;

A bifunctional alkylenic chain, optionally containing 1 or 2 nitrogen atoms, according to the meaninings of R$^2$ and R$^3$ taken together, is a group which forms, with the two adjacent carbon atoms, a six membered aromatic heterocyclic ring, such as:

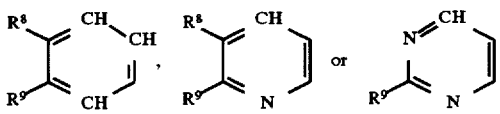

wherein the substituents R$^8$ and R$^9$ has the same meanings as in formula I;

A group of formula =N—(CHR$^{11}$)—X—, —NH—(CHR$^{11}$)—X—or —N=(CR$^{11}$)—X—, is a group which forms, with the adjacent carbon atoms in position 3 and 4,an heterocycle ring such as;

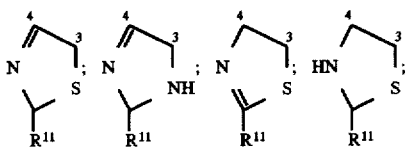

wherein R$^{11}$ is as above defined; obviously, the double bond between the nitrogen atom and the carbon atom in position 4 is only possible when the rifamycin is in the oxidated form.

Di(C$_1$-C$_4$)alkylamino represents an amino moiety substituted with two linear or branched alkyl groups containing 1, 2, 3 or 4 carbon atoms such as: —N—(CH$_3$)$_2$, —N(CH$_3$)(CH$_2$—CH$_3$), —N(CH$_2$—CH$_3$ )$_2$, —N(CH$_3$)(CH$_2$—CH$_2$—

CH$_3$), —N(CH$_2$—CH$_3$)(CH$_2$—CH$_2$—CH$_3$), —N(CH$_2$—CH$_2$—CH$_3$)$_2$, —N(CH$_3$)[CH—(CH$_3$)$_2$], —N(CH$_2$—CH$_3$)[CH—(CH$_3$)$_2$], —N(CH$_3$ )(CH$_2$—CH$_2$—CH$_2$—CH$_3$ ), —N( CH$_2$—CH$_3$ )(CH$_2$—CH$_2$—CH$_2$—CH$_3$), —N( CH$_2$—CH$_2$—CH$_3$ )(CH$_2$—CH$_2$—CH$_2$—CH$_3$), —N( CH$_2$—CH$_2$—CH$_2$—CH$_3$)$_2$, —N(CH$_2$—CH$_2$—CH$_2$—CH$_3$)[CH—(CH$_3$)$_2$].

Pharmaceutically acceptable base addition salts of the compounds of formula I are the rifamycin salts formed with alkali metal, earth-alkali metal, (C$_1$–C$_4$)alkylamines, (C$_1$–C$_4$)alkanolamines or basic aminoacids.

As known in the art, the hydroxy groups linked in positions 1 and 4 on the naphtalenic ring of the compound of formula I, may be both in the reduced form (in such case R$^1$ is hydroxy) or oxidated form (R$^1$ is oxo in this case).

These compounds are derivatives of rifamycin SV and of rifamycin S, respectively. The conversion from one form of rifamycin to the other, and viceversa, is easily carried out by means of oxidating or reducing reactions well known in the art; for instance the oxidation reaction may be carried out with manganese dioxide or potassium hexacyanoferrate(III) in chloroform, while the reducing reaction with ascorbic acid or sodium ascorbate in an hydroalcoholic solution.

The hydroxy moiety in position 1 is also in the oxidated form when the substituent R$^1$ together with R$^2$ (in the compound of formula I) form a group of formula =N—(CHR$^{11}$)—X—, wherein X and R$^{11}$ are as above defined; in this case the formation of the oxo moiety in 1 is a consequence of the double bonding between the nitrogen atom and the carbon atom in position 4.

Therefore, when particular substituents are not present, which would prevent the conversion from the reduced form into the oxidated one, or viceversa, in the continuing of this specification the derivatives of rifamycin S are to be considered as being covertable in the SV form and viceversa.

In the following specification, the term "rifamycins" is intended to comprise within its meanings all the suitable rifamycin and rifamycin-like compounds known in the art, such as rifamycin S, SV, P, the 3- and/or 4-derivatives thereof, and the pharmaceutically acceptable salts thereof.

The rifamycin antibiotic compounds are well known in the art, as being widely used for long time in the treatment of infections caused by Mycobacteria and Gram positive microorganisms and prophylaxis for certain Gram negative infections. The best known member of this antibiotic family is Rifampicin, which is one of the antibiotics of choice in the treatment of tuberculosis, whose main causative agent is *Mycobacterium tuberculosis*.

Rifamycin SV corresponds to the compound of formula I wherein the substituent R at position 36 is replaced by a hydrogen atom, R$^2$ is hydrogen and R$^1$ is hydroxy; rifamycin S is the oxidated form of rifamycin SV, as stated above; rifamycin P is the 4-desoxy-thiazolo-[5,4-c] rifamycin S; rifampicin is the 3-{[(4-methyl-1-piperazinyl)imino]-methyl} rifamycin SV.

The production of rifamycin SV may be obtained by fermenting variant cultures of the strain ATCC 13685 *Nocardia mediterranei* (previously named *Streptomyces mediterranei*, now renamed as *Amycolatopsis mediterranei*); for instance from *Nocardia mediterranei* ATCC 21271, as described in "The Journal of Antibiotics vol. 22, 12, 637, (1969)".

U.S. Pat. No. 3,884,763 discloses a process for preparing rifamycin SV or rifamycin S by aerobically fermenting an aqueous nutrient medium containing a strain of *Micromonospora chalcea* ATCC 21994.

Rifamycin S and SV may also be obtained by chemical modification of the rifamycin B as described in U.S. Pat. No. 3,301,753. Rifamycin B was first obtained as a component of a rifamycin complex by fermenting the *Streptomyces mediterranei* strain ATCC 13685 as described in U.S. Pat. No. 3,150,046; rifamycin B may also be obtained as a single component by adding sodium ethyl barbiturate to the culture medium of *Streptomyces mediterranei* strain ATCC 13685, as described in U.S. Pat. No. 2,988,490 or by fermenting a variant culture of the strain ATCC 13685, i.e. the strain ATCC 21796, as described in U.S. Pat. No. 3,871,965.

Rifamycin P may be obtained either by fermentation of *Streptomyces mediterranei* ATCC 31064, ATCC 31065, ATCC 31066, as disclosed in U.S. Pat. No. 4,263,404, or by chemical modification of rifamycin S, as described in U.S. Pat. No. 4,144,234.

U.S. Pat. No. 4,880,789 discloses the preparation of the 2'-N,N-dialkylamino derivatives of rifamycin P, by treating rifamycin P with dialkylamine in ethyl acetate; such derivatives may also be obtained by treating the 3-bromorifamycin S with N,N-dialkylthiourea, as described by "Cavalleri B. et al., J. of Med. Chem., 1990, 33, 1470–1476".

Rifampicin, which is a rifamycin SV bearing a [(4-methyl-1-piperazinyl)-imino]methyl group in position 3, may be obtained by reacting rifamycin SV with N-methylene-t-butylamine (obtained by reacting formaldehyde with t-butylamine) in the presence of manganese dioxide and then with 1-amino-4-methyl piperazine, as described in U.S. Pat. No. 3,542,762.

Pharmaceutically acceptable salts of rifamycins are also well known in the art, and are easily obtainable by contacting the unsalified rifamycin derivative with the desired base.

For instance, U.S. Pat. No. 3,301,753 discloses the alkali and earth-alkali metal salts of rifamycin SV; U.S. Pat. No. 4,312,866 discloses the preparation of rifamycin SV salts with basic aminoacids, such as arginine, lysine and histidine.

The reaction of 25-O-Deacetyl-3-morpholino rifamycin S-21,23-acetonide with malonic acid was described by W. Wehrli et al. (Journal of Antibiotics, Tokyo, 1987; 40, 1733). The obtained 25-O-Deacetyl-25-O-malonic acid-3-morpholino rifamycin S-21,23-acetonide was further reacted with hydroxybenzotriazole in THF and then with 3-hydroxymethyl-1-methylpiperidine in dicyclohexilcarbodiimmide, thus obtaining the 36-[[(1-methyl-3-piperidinyl)methoxy]carbonyl]-3-morpholino rifamycin S.

25-O-deacetyl-25-O-propionyl and 25-O-deacetyl-25-O-pyvaloyl derivatives of rifamycin are described by Kump W. et al., Helv. Chem. Acta, 1973, 56, 2323.

It is known in the art that prolongated and extensive use of an antibiotic substance in the treatment of infections has the general drawback of the development of mutant strains of the pathogenic microorganism, which strains may show resistance against the specific antibiotic. It would therefore be desirable to produce new antibiotic substances, which are active both against the main causative agent, as well as against the mutant strains thereof which have developed resistance against the original antibiotic.

With the present invention, new antibiotic derivatives of rifamycin are provided which are mainly active against gram positive bacteria and gram positive as well as gram negative anaerobes, and show anti-microbial activity against rifamycin resistant strains.

Preferred compounds of formula I are those compounds wherein:

R is, halo, hydroxy, (C$_1$–C$_4$)acyloxy, (C$_1$–C$_4$)alkoxy, (C$_1$–C$_4$)alkylthio, di(C$_1$–C$_4$)alkylamino or a group of formula:

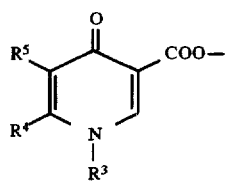

wherein:

$R^3$ represents $(C_1-C_4)$alkyl or $(C_3-C_6)$cycloalkyl;
$R^4$ represents a group of formula

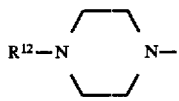

wherein $R^{12}$ represents hydrogen or $(C_1-C_4)$alkyl;
$R^5$ is hydrogen or halo;
or $R^4$ together with $R^5$ form a bifunctional alkylenic chain, optionally containing 1 or 2 nitrogen atoms, of the following formula:

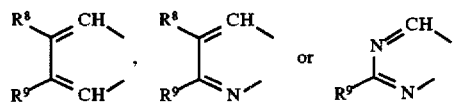

wherein $R^9$ represents $(C_1-C_4)$alkyl, a group of formula,

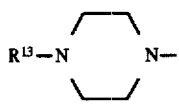

wherein $R^{13}$ is hydrogen or $(C_1-C_4)$alkyl, or a group of formula

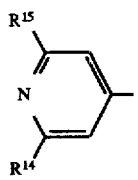

wherein $R^{14}$ and $R^{15}$ independently represent hydrogen or $(C_1-C_4)$alkyl;
$R^1$ is hydroxy in the reduced form or oxygen in the oxydated form;
$R^2$ represents hydrogen, a six membered heterocyclic ring containing one or two heteroatoms selected from oxygen, nitrogen and sulfur, wherein one of the carbon or nitrogen atoms of the ring is optionally substituted by a $(C_1-C_4)$alkyl moiety, or a group of formula:

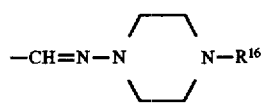

wherein $R^{16}$ represents $(C_1-C_4)$alkyl or $(C_5-C_6)$ cycloalkyl;
or $R^1$ and $R^2$ taken together form a group of formula —N=CR$^{11}$—S— wherein $R^{11}$ represents hydrogen, $(C_1-C_4)$alkyl or di$(C_1-C_4)$alkylamino.

Among the above compounds, further preferred compounds are those of formula I wherein:

R is propyl, butyl, octyl, fluoro, bromo, chloro, iodo, hydroxy, formyl, acetyl, thiomethyl diethylamino or a group of formula:

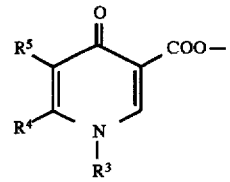

wherein:

$R^3$ is ethyl or cyclopropyl, $R^4$ is 4-methyl-1-piperazinyl and $R^5$ is hydrogen;
or $R^4$ together with $R^5$ form a bifunctional alkylenic chain, optionally containing 1 or 2 nitrogen atoms, of formula:

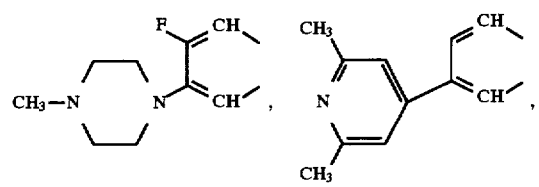

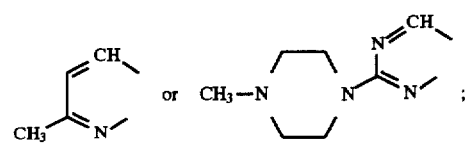

$R^1$ is hydroxy in the reduced form or oxygen in the oxydated form;
$R^2$ is hydrogen, 4-morpholinyl, {[(4-methyl-1-piperazinyl)imino]methyl} or {[(4-cyclopentyl-1-piperazinyl)imino]methyl};
or $R^1$ and $R^2$ together form a group of formula

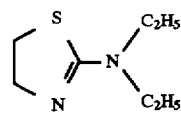

Particularly preferred compounds are those compounds of formula I wherein:

R is bromo, chloro, iodo, hydroxy or a group of formula:

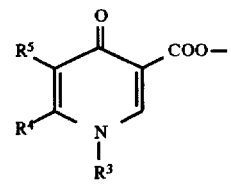

wherein:

$R^3$ is ethyl, $R^4$ is 4-methyl-1-piperazinyl and $R^5$ is hydrogen;
or $R^4$ together with $R^5$ form a bifunctional alkylenic chain of formula:

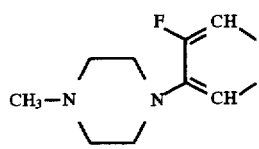

$R^1$ is hydroxy in the reduced form or oxygen in the oxydated form and $R^2$ is hydrogen, 4-morpholinyl or {[(4-methyl-1-piperazinyl)-imino]methyl}.

Representative examples of the compounds of the invention are:

36-bromorifamycin S
36-fluororifamycin S
36-chlororifamycin S
36-iodorifamycin S
36-methylthiorifamycin S
36-ethylthiorifamycin S
36-hydroxyrifamycin S
36-methoxyrifamycin S
36-ethoxyrifamycin S
36-formylrifamycin S
36-acetylrifamycin S
36-diethylaminorifamycin S
3,36-dibromorifamycin S
3,36-dichlororifamycin S
36-bromo-3-cyanorifamycin S
36-butyl-3-bromorifamycin S
36-hydroxy-3-cyanorifamycin S
36-methylthio-3-cyanorifamycin S
36-chloro-3-methylrifamycin S
36-bromo-3-ethylrifamycin S
36-acetyl-3-ethoxyrifamycin S
36-chloro-3-butoxyrifamycin S
36-bromo-3-methylthiorifamycin S
36-methylthio-3-ethoxycarbonylrifamycin S
36-butyl-3-(dimethylamino)rifamycin S
36-chloro-3-(ethylpropylamino)rifamycin S
36-bromo-3-(diethylamino)rifamycin S
36-butyl-3-ethylthiorifamycin S
36-chloro-3-cyanorifamycin S
36-methylthio-3-(dimethylaminomethylene)rifamycin S
36-bromo-3-(ethylmethylaminomethylene)rifamycin S
36-bromo-3-(4-morpholinyl)rifamycin S
36-bromo-3-(4-(2-ethyl)-morpholinyl)rifamycin S
36-chloro-3-(4-(2-ethyl)-morpholinyl)rifamycin S
36-bromo-3-(1-piperidyl)rifamycin S
36-bromo-3-(3-(1-methyl)piperidyl)rifamycin S
36-iodo-3-(1-(3-methyl)-piperidyl)rifamycin S
36-chloro-3-(1-(3-methyl)-piperidyl)rifamycin S
36-acetyl-3-(1-piperazinyl)rifamycin S
36-bromo-3-(1-(3-methyl)piperazinyl)rifamycin S
36-hydroxy-3-(1-(3-methyl)piperazinyl)rifamycin S
36-fluoro-3-(4-morpholinyl)rifamycin S
36-chloro-3(4-morpholinyl)rifamycin S
36-methylthio-3-(4-morpholinyl)rifamycin S
36-hydroxy-3-(4-morpholinyl)rifamycin S
36-formyl-3-(4-morpholinyl)rifamycin S
36-acetyl-3-(4-morpholinyl)rifamycin S
36-diethylamino-3-(4-morpholinyl)rifamycin S
36-bromo-3-(4-thiomorpholinyl)rifamycin S
36-iodo-3-(4-thiomorpholinyl)rifamycin S
36-bromo-3-(4-(3-ethyl)thiomorpholinyl)rifamycin S
36-fluoro-3-(3-thiomorpholinyl)rifamycin S
36-chloro-3-(2-thiomorpholinyl)rifamycin S
36-methylthio-3-(4-thiomorpholinyl)rifamycin S
36-formyl-3-(4-thiomorpholinyl)rifamycin S
36-bromorifamycin P
36-fluororifamycin P
36-chlororifamycin P
36-iodorifamycin P
36-hydroxyrifamycin P
36-methylthiorifamycin P
36-formylrifamycin P
36-acetylrifamycin P
36-diethylaminorifamycin P
36-bromo-2'-(methyl)rifamycin P
36-fluoro-2'-(diethylamino)rifamycin P
36-chloro-2'-(diethylamino)rifamycin P
36-formyl-2'-(diethylamino)rifamycin P
36-bromo-2'-(diethylamino)rifamycin P
36-hydroxy-2'-ethylrifamycin P
36-chloro-2'-(ethylamino)rifamycin P
36-bromo-2'-butylrifamycin P
36-acetyl-2'-(butylamino)rifamycin P
36-bromo-2'-(ethylmethylamino)rifamycin P
36-chloro-2'-ethylrifamycin P
36-[(1-ethyl-6-fluoro-1,4-dihydro-7-(4-methyl-1-piperazinyl)-4-oxo-3-quinolinyl)carbonyloxy] rifamycin S
36-{[1-ethyl-1,4-dihydro-7-methyl-4-oxo-1,8-naphthyridin-3-yl)carbonyloxy} rifamycin S
36-{[8-ethyl-5,8-dihydro-2-(4-methyl-1-piperazinyl)-5-oxopyrido[2,3-d]pyrimidin-6-yl]carbonyloxy} rifamycin S
36-{[1-cyclopropyl-6-fluoro-1,4-dihydro-7-(2,6-dimethyl-4-pyridinyl)-4-oxo-3-quinolinyl] carbonyloxy} rifamycin S
36-{[1-ethyl-1,4-dihydro-6-(4-methyl-1-piperazinyl)-4-oxo-3-pyridinyl]carbonyloxy} rifamycin S
36-[(1-ethyl-6-fluoro-1,4-dihydro-7-(4-methyl-1-piperazinyl)-4-oxo-3-quinolinyl)carbonyloxy]-3-(4-morpholinyl) rifamycin S
36-{[1-ethyl-1,4-dihydro-7-methyl-4-oxo-1,8-naphthyridin-3-yl)carbonyloxy}-3-(4-morpholinyl) rifamycin S
36-{[8-ethyl-5,8-dihydro-2-(4-methyl-1-piperazinyl)-5-oxopyrido[2,3-d]pyrimidin-6-yl]carbonyloxy}-3-(4-morpholinyl) rifamycin S
36-{[1-cyclopropyl-6-fluoro-1,4 -dihydro-7-(2,6-dimethyl-4-pyridinyl)-4-oxo-3-quinolinyl] carbonyloxy}-3-(4-morpholinyl) rifamycin S
36-{[1-ethyl-1,4-dihydro-6-(4-methyl-1-piperazinyl)-4-oxo-3-pyridinyl]carbonyloxy}-3-(4-morpholinyl) rifamycin S
36-[(1-ethyl-6-fluoro-1,4-dihydro-7-(4-methyl-1-piperazinyl)-4-oxo-3-quinolinyl)carbonyloxy]-3{[(4-methyl-1-piperazinyl)imino]methyl} rifamycin SV 36-{[1-ethyl-1,4-dihydro-7-methyl-4-oxo-1,8-naphthyridin-3-yl) carbonyloxy}-3-{[(4-methyl-1-piperazinyl)imino]methyl} rifamycin SV 36-{[8-ethyl-5,8-dihydro-2-(4-methyl-1-piperazinyl)-5-oxopyrido[2,3-d]pyrimidin-6-yl]carbonyloxy}-3-{[(4-methyl-1-piperazinyl)imino]methyl} rifamycin SV 36-{[1-cyclopropyl-6-fluoro-1,4-dihydro-7-(2,6-dimethyl-4-pyridinyl)-4-oxo-3-quinolinyl] carbonyloxy}-3{[(4-methyl-1-piperazinyl)imino] methyl} rifamycin SV 36-{[1-ethyl-1,4-dihydro-6-(4-methyl-1-piperazinyl)-4-oxo-3-pyridinyl]carbonyloxy}-3{[(4-methyl-1-piperazinyl)imino]methyl} rifamycin SV 36-[(1-ethyl-6-fluoro-1,4-dihydro-7-(4-methyl-1-piperazinyl)-4-oxo-3-quinolinyl)carbonyloxy]-3{[(4-cyclopentyl-1-piperazinyl)imino]methyl} rifamycin SV 36-{[1-ethyl-1,4-dihydro-7-methyl-4-oxo-1,8-naphthyridin-3-yl) carbonyloxy}-3-{[(4-cyclopentyl-1-piperazinyl)imino]methyl} rifamycin SV 36-{[8-ethyl-5,8-dihydro-2-(4-methyl-1-piperazinyl)-5-oxopyrido[2,3-d]pyrimidin-6-yl]carbonyloxy}-3-{[(4-cyclopentyl-1-piperazinyl)imino]methyl} rifamycin SV 36-{[1-cyclopropyl-6-fluoro-1,4-dihydro-7-(2,6-dimethyl-4-pyridinyl)-4-oxo-3-quinolinyl] carbonyloxyl}-3{[(4-cyclopentyl-1-piperazinyl)imino] methyl} rifamycin SV 36-{[1-ethyl-1,4-dihydro-6-(4-methyl-1-piperazinyl)-4-oxo-3-pyridinyl]carbonyloxy}-3{[(4-cyclopentyl-1-piperazinyl)imino]methyl} rifamycin SV 36-{[1-ethyl-1,4-dihydro-6-(dimethylamino)-4-oxo-3-pyridinyl]carbonyloxy}-3{[(4-cyclopentyl-1-piperazinyl)imino]methyl} rifamycin SV 36-{[1-ethyl-1,4-dihydro-6-(dimethylamino)-5-fluoro-4-oxo-3-pyridinyl]carbonyloxy}-3-{[(4-cyclopentyl-1-piperazinyl)imino]methyl} rifamycin SV 36-{[1-ethyl-1,4-dihydro-6-(4-methyl-1-piperazinyl)-5-fluoro-4-oxo-3-pyridinyl]carbonyloxy}-3-{[(4-cyclopentyl-1-piperazinyl)imino]methyl} rifamycin SV 36-[(1-ethyl-6-fluoro-1,4-dihydro-7-(4-methyl-1-piperazinyl)-4-oxo-3-quinolinyl)carbonyloxy]-2'-(diethylamino) rifamycin P 36-{[1-ethyl-1,4-dihydro-7-methyl-4-oxo-1,8-naphthyridin-3-yl)carbonyloxy}-2'-(diethylamino) rifamycin P 36-{[8-ethyl-5,8-dihydro-2-(4-methyl-1-piperazinyl)-5-oxopyrido[2,3-d]pyrimidin-6-yl]carbonyloxy}-2'-(diethylamino) rifamycin P 36-{[1-cyclopropyl-6-fluoro-1,4-dihydro-7-(2,6-dimethyl-4-pyridinyl)-4-oxo-3-quinolinyl] carbonyloxy}-2'-(diethylamino) rifamycin P 36-{[1-ethyl-1,4-dihydro-6-(4-methyl-1-piperazinyl)-4-oxo-3-pyridinyl]carbonyloxy}-2'-(diethylamino) rifamycin P.

The preferred pharmaceutically acceptable salts of the compounds of formula I are the rifamycin salts formed with alkali metal or basic aminoacids; most preferred are the salts with sodium, arginine, lysine or histidine.

A-further object of the present invention is to provide a process for preparing the compounds of general formula I. With said process it is also possible to prepare the rifamycin derivatives of formula I wherein R is a $(C_1-C_8)$alkyl group.

Thus, only when referring to the preparation method, the meaning of R will encompass also this further group.

All the suitable rifamycins known in the art may in general be used as starting materials for producing the compounds of the present invention.

Further chemical modifications of the above rifamycins, which allow to obtain the suitable starting material for producing the compounds of the invention, are known in the art, or can easily be carried out by the skilled man, according to the common general knowledge.

For instance, U.S. Pat. No. 4,086,225 discloses the preparation of 4-desoxy-imidazolo[4,5-c] rifamycin derivatives from Rifamycin S; U.S. Pat. No. 4,880,789 describes the preparation of 2'-dialkylamino derivatives of Rifamycin P.

Alternatively, 36-substituted rifamycin S or SV may be obtained according to the present process while the desired substituents are introduced in the other positions of the molecule only afterwards. This procedure is preferably followed when said further substituents would prevent the normal course of reaction or could itself undergo unwanted chemical modifications during the preparation of the 36-derivatives according to the process of the present invention.

For instance the presence of the group —CH=N—$R^{10}$, wherein $R^{10}$ is as defined in formula I, in position 3 would prevent the protection of positrons 21 and 23 of the rifamycin molecule (i.e. the formation of the cyclic-21,23-(1-methylethylidene acetal)) which protection is necessary for obtaining the starting material of the present process. Therefore, after the desired 36-derivative of rifamycin SV has been obtained as described hereinafter, it will be further reacted, for instance with N-methylene-t-butylamine in the presence of t-butylamine and manganese dioxide and then with a compound of formula $NH_2-R^{10}$, in order to insert at the 3-position the desired substituent of formula —CH=N—$R^{10}$.

According to the common general knowledge, the skilled man will decide whether introduce such further substituents before or after the process of the present invention, depending on the specific characteristics of the desired substituent.

The compounds of formula I may be obtained by reacting the corresponding 25-O-deacetylated rifamycin with a suitable malonic acid derivative in the presence of a condensing agent.

The deacetylation in position 25 of rifamycin, is easily achieved according to the common hydrolysis techniques known in the art; for instance, U.S. Pat. No. 4,188,321, discloses the preparation of 25-O-Deacetylrifamycin S, or derivatives thereof, by reacting rifamycin S, or derivatives thereof, with sodium hydroxide or sodium bicarbonate, respectively.

For the process of the invention, the above rifamycin starting materials may not be reacted as such, but has to be protected on the positions 21 and 23, before reacting it. Such protection is performed according to the methods known in the art for protecting geminal hydroxy groups and results in a ciclyzation of the two oxygen atoms of the hydroxy functions in position 21 and 23. As a general procedure, it is preferred to perform the deacetylation in position 25 after the protection reaction.

For instance, 25-O-deacetylrifamycin S cyclic-21,23-(1-methylethylidene acetal)—wherein $R^1$ is oxo and $R^2$ is hydrogen—may be prepared by reacting rifamycin S with acetone and anhydrous cupric sulfate or with 2,2-dimethoxypropane and sulfuric acid, and then hydrolyzing with NaOH, according to "W. Kump and H. Birchel, Helv.Chim. Acta, 1973, 56, 2323"; the preparation of 25-O- deacetyl-3-(4-morpholinyl)rifamycin S cyclic-21,23-(1-methyl-ethylidene acetal)—wherein $R^1$ is oxo and $R^2$ is morpholinyl—by reacting 3-(4-morpholinyl)rifamycin S with 2,2-dimethoxypropane in anhydrous acetone and then hydrolyzing with NaOH, is described in "W. Wehrli et al., Journal of antibiotics, 1987, 40, 1733".

The protected rifamycin P may be prepared by reacting the 25-O-Deacetylrifamycin S cyclic-21,23-(1-methylethylidene acetal) with N-bromosuccinimide and 1,1-diethylthiourea in dimethylformamide, thus obtaining the corresponding 25-O-Deacetylrifamycin P cyclic-21,23-(1-methyl-ethylidene acetal).

The process of the present invention therefore comprises:
a) reacting a compound of general formula II wherein $R^1$ and $R^2$ have the same meanings as in formula I, with the proviso that $R^2$ is not a group of formula:
—CH=N—$R^{10}$,
with a malonic acid derivative of formula III:

wherein R is as above defined, in the presence of a condensing agent;
b) removing the protecting group in positions 21 and 23 by means of an acidic cleavage of the acetonidic moiety;
c) contacting the deprotected compound with a cuprous salt or oxide or a mixture thereof in the presence of an inert organic solvent.

According to the first step of the above process one of the two malonic carboxylic moieties reacts with the hydroxy moiety in position 25 of the compound of formula II, thus forming an ester moiety in such position. The second carbon atom of this moiety is conventionally numbered as $C^{36}$.

This reaction is generally conducted in the presence of an inert organic solvent which do not unfavorably interfere with the reaction course and is capable of at least partially solubilizing the antibiotic material.

Said inert organic solvents are those commonly used in the art and comprise alkylamides, alkylnitriles, saturated linear or cyclic ethers, glycol ethers, phosphoramides, sulfoxides, chlorinated solvents or mixtures thereof.

Preferred inert organic solvents are: dimethylformamide, acetonitrile, dimethoxyethane, tetrahydrofuran (THF), hexamethyl-phosphoramide, dimethylsulfoxide, chloroform and dichloroethane or mixtures thereof; most preferred is tetrahydrofuran.

The condensing agent may be any substance commonly used in the art for the esterification reactions selected from carboxydiimides, dialkylaminopyridines, carbonylimidazoles, triphenilphosphine in carbon tetrachloride, substituted dithiocarbonates and diphenylphosphorilazides. Examples of said condensating agents are: 4-dimethylaminopyridine, N,N'-carboyl-bis imidazole, S,S'-bis-1-(phenyl-1H-tetrazol-5-yl)-dithiocarbonate and 1,3-Dicyclohexylcarbodiimmide (DCC).

Preferred condensing agents are carboxydiimmides derivatives, 1,3-Dicyclohexylcarbodiimmide being the most preferred one.

The above reaction is preferably conducted at temperatures from about 0° C. to 35° C., while the reaction time may vary from 1 to 2 hours. More preferably, the mixture is reacted at 0° C. for about 15 minutes and then for about one hour at room temperature.

The removal of the acetonidic moiety bridging positions 21 and 23 is performed under mild acidic conditions in the presence of an inert organic solvent, as above defined. The acids commonly used for the cleavage of such moiety can be here conveniently utilized; these acids have to be in diluted form, to avoid the demolition of the substrate. Suitable acids are mineral acids (e.g. hydrochloric acid, sulfuric acid) or organic sulfonic acids (e.g. p-toluensulfonic acid), the preferred one being sulfuric acid.

The reaction is conducted between 30° C. and 50° C., while the reaction time may vary from 14 to 18 hours. It is generally preferred to carry it out at a temperature of about 40° C. for about 16 hours.

Step c of the present process permits the removal of the free carboxy moiety linked to the $C^{36}$,for obtaining the corresponding compound of general formula 1.

For the decarboxylation reaction any salt or oxide or a mixture thereof containing the cuprous ion can be employed. Examples of these compounds are: $Cu_2O$, $Cu_2S$, CuCl, CuBr and $Cu_2SO_4$, most preferred being cuprous oxide.

Although all the cuprous compounds work well as decarboxylating agents, the use of CuCl or CuBr should be avoided when the malonic acid substrate is substituted with a bromine or chlorine atom respectively, because of a possible ion exchange side reaction. Of course, this problem arises only if the product has to be obtained in a pure form, while if a mixture of halogenated derivatives is desired, the use of CuCl or CuBr in this specific case is also possible.

The inert organic solvent to be used should be capable of at least partially solubilizing the antibiotic material and should not unfavorably interfere with the reaction course. The skilled man would be able to choose the most appropriate solvent among those commonly used in the art. Suitable solvents are those previously listed and, among those, the preferred solvent for this reaction is acetonitrile.

The reaction temperature is from 50° C. to 75° C., preferably from 60° C. to 70° C.

The reaction time may vary depending on the nature of substituent on the malonic moiety. For the most reactive compounds it is about one hour, while for the less reactive ones it raises up to 20 hours.

Although with the above described process it is possible to directly obtain the new rifamycin derivatives of the invention, some of these compounds are preferably obtained according to an alternative procedure, which comprises contacting a 36-halo rifamycin derivative obtained according to the above process with an appropriate reactant, in order to insert the desired substituent R in the position 36.

With this alternative procedure it is therefore not necessary to prepare the specific substituted malonic acid derivative of formula III according to each meaning of R, but starting from halo-malonic acid most of the compounds of the invention are easily obtainable.

This procedure is particularly suitable when the desired substituent R in the position 36 of rifamycin is hydroxy, iodo, (C₁–C₄)acyloxy, (C₁–C₄)alkylamino, di(C₁–C₄)alkylamino or a group of formula:

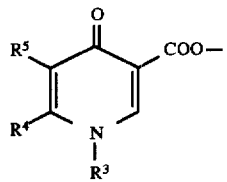

Such further reactions for preparing these new rifamycin derivatives are all subsequent to the previous steps a to c described above and may be either alternative or subsequent one to each other; these further steps are illustrated hereinafter for each kind of substituent.

When R is iodo, the 36-chloro or 36-bromo rifamycin derivative obtained according to steps a to c of the above process, is contacted with an acetonic solution of an alkali metal iodide.

The halogen ion exchange reaction for obtaining the 36-iodo rifamycin derivatives is easily accomplished by contacting the corresponding 36-halo rifamycin derivative with a metal alkali iodide, preferably sodium iodide, in the presence of acetone, as commonly known in the art.

Such reaction is generally conducted at room temperature for about 3 to 5 hours.

When R is (C₁–C₄)acyloxy, the 36-chloro, -bromo or -iodo rifamycin derivative obtained as above described, is contacted with a (C₁–C₄)acylate salt, in the presence of an inert organic solvent.

The (C₁–C₄)acylate salt is preferably an alkali metal, most preferred is potassium, or a silver salt, while the inert organic solvent is selected among those listed above, preferably being anhydrous dimethylformamide.

The reaction is generally conducted at room temperature for about 16 to 26 hours.

When R is (C₁–C₄)alkylamino or (C₁–C₄)dialkylamino the 36-chloro, -bromo or -iodo rifamycin derivative obtained as above described, is contacted with the correspondent alkyl or dialkylamine in the presence of an inert organic solvent.

The inert organic solvent is preferably tetrahydrofuran and the reaction is generally conducted at room temperature for about 2 to 6 hours.

When R is hydroxy, the 36-formyloxy rifamycin derivative obtained as above described, is hydrolized underbasic conditions.

The hydrolisis is conducted in an hydroalcoholic solution under mild basic conditions, at room temperature, for about 10 to 16 hours. Preferably, the reaction is performed with potassium bicarbonate in a water/methanol mixture (rate from 1+2 to 1+3 v/v).

Finally, when R is a group of formula

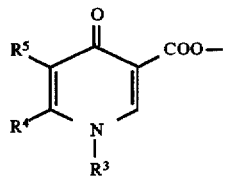

the 36-chloro, -bromo or -iodo rifamycin derivative obtained as above described is contacted with a salt of a 4-oxo-3-pyridinyl carboxylic acid derivative of general formula IV

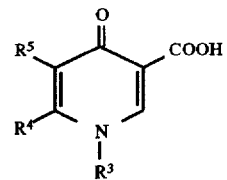

wherein $R^3, R^4$ and $R^5$ are as defined in formula I, in the presence of an inert organic solvent.

Preferably a litium, sodium, potassium or silver salt of the 4-oxo-3-pyridinyl carboxylic acid derivative is employed.

The 4-oxo-3-pyridinyl carboxylic acid derivatives, may be commercially available compounds such as Pefloxacin®, Nalidixic acid or N-methyl-pipemidic acid, known compounds such as those described in U.S. Pat. No. 5,075,319, or new compounds derived from the compounds of general formula Va or Vb:

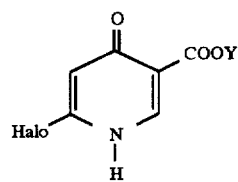

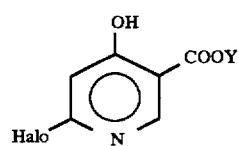

wherein Hal represents chloro or bromo and Y is hydrogen or lower alkyl. The compounds of formula IVa and IVb may be prepared by saponification of the corresponding 4,6-di-halo-nicotinic acid or lower alkyl 4,6-di-halo-nicotinate, as disclosed in Israeli Patent 44327/2.

The compounds of formula Va are preferably reacted first with an alkylating agent, so to obtain the corresponding N-(C₁–C₄)alkyl or N-(C₃–C₆)cycloalkyl derivatives; afterwards this N-alkylated compound is reacted with a suitable amine in order to substitute the halogen with the desired moiety of formula —NR⁶R⁷, wherein $R^6$ and $R^7$ are as defined in formula I.

For instance, suitable starting materials for the process of the present invention may be prepared by reacting a N-alkyl derivative of a compound of general formula IVa with N-methylpiperazine.

The novel compounds of general formula VI

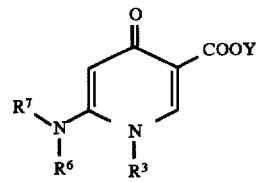

wherein Y is hydrogen or (C₁–C₄)alkyl and $R^3$, $R^6$ and $R^7$ have the same meanings as in formula I, also fall within the scope of the present invention.

The inert organic solvent that may be used in the present process should be capable of at least partially solubilizing the antibiotic material and should not unfavourably interfere with the reaction course. The skilled man would be able to choose the most appropriate solvent among those commonly used in the art, partcularly in view of the teachings of the present disclosure. Suitable solvents are those listed before when dealing with reaction of the malonic acid derivative with rifamycin. Particularly preferred is dimethylformamide.

The reaction is conducted generally at a temperature between 15° C. and 40° C.

The reaction time may vary from 10 to 24 hours.

Preferably, the salt of the compond of formula IV is first added to the inert organic solvent and stirred at room temperature for about 30 minutes, optionally in the presence of an activated molecular sieve, such as Union Carbide type 4 Å(FLUKA); afterwards, the suitable 36-chloro, -bromo or -iodo rifamycin derivative is added to the solution and the mixture is stirred for from 14 to 20 hours at room temperature.

Preferred 36-halo rifamycin derivatives which may be employed for the present process are the 36-iodo derivatives, whilst preferred carboxylic acid salt is potassium salt.

Separation and purification of the reaction products obtained according to the various steps of the present process is made according to the known per se techniques.

The separation of the reaction products is preferably accomplished by means of extraction with water-immiscible organic solvents or by adding non-solvents.

The term "water-immiscible solvent" as used in this application, is intended to have the meaning currently given in the art to this term and refers to solvents that at the conditions of use are slightly miscible or practically immiscible with water in a reasonably wide concentration range, suitable for the intended use.

Examples of water-immiscible organic solvents that can be used in the extraction of the antibiotic substances of the invention from an aqueous phase are: the usual hydrocarbon solvents which may be linear, branched or cyclic such as hexane or cyclohexane; halogenated hydrocarbons such as chloroform, carbon tetrachloride, dichloromethane, dichloroethane, fluorobromoethane, dibromoethane, trichloropropane, chlorotrifluorooctane and the like; aromatic hydrocarbons such as benzene, toluene, xylene and the like; esters of at least four carbon atoms, such as ethyl acetate, propyl acetate, ethyl butyrate, and the like; alkanols of at least four carbon atoms which may be linear, branched or cyclic such as butanol, 1-pentanol, 2-pentanol, 3-pentanol, 1-hexanol, 2-hexanol, 3-hexanol, 3,3-dimethyl-1-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol; straight or branched alkyl ethers and mixture thereof such as petroleum ether, ethyl ether, propyl ether, butyl ether, etc; and mixtures or functional derivatives thereof; the preferred one being ethyl acetate.

Examples of precipitating agents are petroleum ether and lower alkyl ethers, such as ethyl ether, propyl ether and butyl ether; the preferred one being petroleum ether.

Purification of the reaction products may be obtained by precipitation with non-solvents or by chromatographic techniques.

Precipitating agents suitable for purification are those listed above.

The chromatographic techniques suitable for purifying the reaction products of the present process are those commonly known in the art and comprise partition chromatography, reverse-phase partition chromatography, ion-exchange chromatography, flash chromatography, affinity chromatography, HPLC techniques and the like. the preferred one being flash chromatography. Preferably the purification of the residue is accomplished by means of flash-chromatography; particulary preferred as stationary phase is silica gel, while preferred eluent is methanol in dichloroethane.

The antimicrobial activity of the compounds of the present invention was demonstrated by a series of standard in vitro tests.

The minimal inhibitory concentration (MIC) for the microorganisms was determined by broth microdilution methodology. Inocula were approximately $10^4$ colony-forming units per ml (CFU/ml), except for *Bacteroides fragilis*, *Clostridium perfringens* and *Propionibacterium acnes* ($10^5$ CFU/ml).

Incubation was at 37° C. *Neisseria gonorrhoeae* and *Haemophilus influenzae* were incubated in 5% carbon dioxide in air; *C. perfringens*, *P. acnes* and *B. fragilis* in nitrogen-carbon dioxide-hydrogen (80:10:10); other organisms in air. Incubation times were 48 hours for *N. gonorrhoeae*, *H. influenzae*, *P. acnes* and *B. fragilis*; 20–24 hours for other organisms.

The growth media were: Iso-Sensitest broth (Oxoid) for staphylococci, *Enterococcus faecalis*, *Escherichia coli*, *Proteus vulgaris*, *Klebsiella pneumoniae*, and *Pseudomonas aeruginosa*; Todd Hewitt broth (Difco) for streptococci; GC Base broth (Difco)+1% (v/v) IsoVitaleX (BBL) for *N. gonorrhoeae*; Brain Heart Infusion broth (Difco)+1% (v/v) Supplement C (Difco) for *H. influenzae*; Wilkins-Chalgren broth (Difco) for *C. perfringens*, *P. acnes* and *B. fragilis*.

The following table I reports the antimicrobial activity of representative compounds of the invention.

TABLE I

| STRAIN | Internal code | MIC of the compounds (µg/ml) | | | | | | | | | | |
|---|---|---|---|---|---|---|---|---|---|---|---|---|
| | | C1 | C2 | C3 | C4 | C8 | C9 | C10 | C12 | C13 | C15 | C22 |
| *Staphylococcus aureus* | L165 | 0.004 | 0.015 | 0.004 | 0.008 | 0.002 | 0.06 | 0.06 | 0.03 | 0.002 | 0.002 | 0.06 |
| *Staph. aureus* rifa-r[1] | L721 | 0.25 | n.t. | 1 | n.t. | 0.5 | 8 | n.t. | n.t. | 0.25 | 2 | 0.13 |
| *Staph aureus* rifa-r[2] | L1282 | 2 | 64 | 16 | 32 | 0.5 | >128 | 32 | 32 | 4 | 4 | 1 |
| *Staph aureus* Smith | L819 | n.t. | n.t. | n.t. | n.t. | n.t. | n.t. | n.t. | n.t. | n.t. | n.t. | 0.06 |
| *Staph epidermidis* ATCC 12228 | L147 | 0.004 | 0.015 | 0.008 | 0.001 | 0.001 | 0.06 | 0.06 | 0.008 | 0.001 | 0.001 | 0.06 |
| *Staph haemolyticus* rifa-r[2] | L602 | 32 | ≧128 | 64 | 128 | 16 | ≧128 | 64 | 64 | 32 | 4 | 0.5 |
| *Streptococcus pyogenes* | L49 | 0.03 | 0.008 | 0.016 | 0.008 | 0.06 | 0.13 | 0.015 | 0.06 | 0.008 | 0.03 | 0.06 |
| *Strept. pneumoniae* | L44 | 0.03 | 0.015 | 0.03 | 0.002 | 0.03 | 0.13 | 0.03 | 0.03 | 0.008 | 0.016 | 0.06 |
| *Enterococc. faecalis* ATCC 7080 | L149 | 1 | 1 | 0.25 | 0.5 | 0.5 | 2 | 2 | 0.25 | 0.13 | 0.5 | 2 |

TABLE I-continued

| | | | | | | | | | | | |
|---|---|---|---|---|---|---|---|---|---|---|---|
| Propionibact. acnes ATCC 6919 | L1014 | 0.016 | 0.13 | 0.03 | 0.06 | 0.004 | 0.06 | 0.13 | 0.5 | 0.03 | 0.016 | n.t. |
| Clostridium perfringens | L290 | 0.0003 | n.t. | 0.0003 | n.t. | 0.001 | n.t. | n.t. | n.t. | 0.005 | 0.001 | n.t. |
| Bacteroides fragilis ATCC 23745 | L1010 | n.t. | 2 | n.t. | 0.5 | n.t. | 0.13 | 0.5 | 2 | n.t. | n.t. | 0.13 |
| Bacteroides fragilis ATCC 25285 | L1011 | 1 | n.t. | 0.13 | n.t. | 0.03 | n.t. | n.t. | n.t. | 0.5 | 0.03 | n.t. |
| Neisseria gonorrheae | L997 | 1 | 2 | 0.13 | 0.5 | 0.03 | 0.25 | 16 | 1 | 0.25 | 0.03 | 0.25 |
| Moraxella catarr. ATCC 8178 | L76 | 0.008 | n.t. | 0.008 | n.t. | 0.002 | n.t. | n.t. | n.t. | 0.004 | 0.002 | n.t. |
| Haemoph. influenzae ATCC 19418 | L970 | 1 | 2 | 1 | 1 | 0.13 | 0.25 | 4 | 1 | 0.5 | 0.06 | 0.5 |
| Escherichia coli | L47 | 32 | 128 | 32 | 64 | 8 | 16 | 64 | 32 | 16 | 8 | ≧128 |
| Esch. coli K12 hyperpermeable | G1640 | 0.25 | 1 | 0.25 | 0.51 | ≦0.13 | 2 | 1 | ≦0.13 | ≦0.13 | ≦0.13 | n.t. |
| Esch. coli K12 rifa-r$^{(1)}$ | G1064 | >128 | >128 | >128 | >128 | >128 | >128 | ≧128 | >128 | >128 | >128 | n.t. |
| Esch. coli K12 wild type | G210 | n.t. | ≧128 | n.t. | 64 | n.t. | n.t. | 128 | 64 | n.t. | n.t. | n.t. |
| Proteus vulgaris ATCC 881 | L79 | 16 | 32 | 8 | 8 | 8 | 32 | 32 | 8 | 8 | 8 | 64 |
| Klebsiella pneumoniae | L142 | 128 | n.t. | 64 | n.t. | 16 | n.t. | n.t. | n.t. | 64 | 8 | n.t. |
| Pseudomonas aerug. ATCC 10145 | L4 | 32 | 64 | 32 | 32 | 16 | 16 | 32 | 32 | 32 | 16 | 32 |

| | | Internal | MIC of the compounds (µg/ml) | | | | | | | |
|---|---|---|---|---|---|---|---|---|---|---|
| STRAIN | | code | C23 | C24 | C25 | C26 | C27 | C28 | C29 | C30 |
| Staphylococcus aureus | | L165 | 0.06 | 0.06 | 0.06 | 0.06 | 0.03 | 0.06 | 0.03 | 0.016 |
| Staph. aureus rifa-r$^{(1)}$ | | L721 | 0.06 | 0.06 | 0.13 | 0.13 | 0.25 | 0.13 | 0.5 | 0.5 |
| Staph. aureus rifa-r$^{(2)}$ | | L1282 | 1 | 0.13 | 1 | 2 | 16 | 2 | 2 | 1 |
| Staph. aureus Smith | | L819 | n.t. | 0.06 | 0.06 | 0.13 | 0.016 | 0.06 | 0.03 | 0.016 |
| Staph. epidermidis ATCC 12228 | | L147 | 0.06 | 0.008 | 0.13 | 0.06 | 0.016 | 0.06 | 0.03 | 0.016 |
| Staph. haemolyticus rifa-r$^{(2)}$ | | L602 | 4 | 0.13 | 1 | 0.5 | 16 | 4 | 8 | 4 |
| Streptococcus pyogenes | | L49 | 0.004 | 0.06 | 0.03 | 0.03 | 0.008 | 0.016 | 0.016 | 0.016 |
| Strept. pneumoniae | | L44 | 0.004 | 0.008 | 0.016 | 0.03 | 0.008 | 0.008 | 0.016 | 0.008 |
| Enterococc. faecalis ATCC 7080 | | L149 | 0.13 | 0.13 | 2 | 4 | 2 | 8 | 2 | 0.25 |
| Propionibact. acnes ATCC 6919 | | L1014 | 2 | 0.06 | n.t. | 0.13 | 0.03 | 0.06 | 0.06 | 0.03 |
| Clostridium perfringens | | L290 | n.t. | n.t. | n.t. | n.t. | n.t. | n.t. | n.t. | n.t. |
| Bacteroides fragilis ATCC 23745 | | L1010 | 8 | 0.13 | n.t. | n.t. | n.t. | n.t. | n.t. | n.t. |
| Bacteroides fragilis ATCC 25285 | | L1011 | n.t. | n.t. | 2 | 1 | 0.13 | 1 | 0.13 | 0.06 |
| Neisseria gonorrheae | | L997 | 8 | 0.06 | 0.5 | 0.13 | 0.13 | 0.25 | 0.25 | 0.13 |
| Moraxella catharralis ATCC 8178 | | L997 | n.t. | n.t. | n.t. | n.t. | n.t. | n.t. | n.t. | n.t. |
| Haemoph. influenzae ATCC 19418 | | L970 | 2 | 0.13 | 1 | 1 | 0.25 | 2 | 0.25 | 1 |
| Escherichia coli | | L47 | 128 | 16 | 64 | 2 | 32 | 64 | 16 | 16 |
| Esch. coli K12 hyperpermeable | | G1640 | n.t. | n.t. | n.t. | n.t. | n.t. | n.t. | n.t. | n.t. |
| Esch. coli K12 rifa-r$^{(1)}$ | | G1064 | n.t. | n.t. | n.t. | n.t. | n.t. | n.t. | n.t. | n.t. |
| Esch. coli K12 wild type | | G210 | n.t. | n.t. | n.t. | n.t. | n.t. | n.t. | n.t. | n.t. |
| Proteus vulgaris ATCC 881 | | L79 | 128 | 16 | 64 | 2 | 16 | 64 | 128 | 16 |
| Klebsiella pneumoniae | | L142 | n.t. | n.t. | n.t. | n.t. | n.t | n.t. | n.t. | n.t. |
| Pseudomonas aerug. ATCC 10145 | | L4 | >128 | 16 | 128 | 32 | 32 | 128 | >128 | 32 | rifa-r = rifampicin resistant strain; $^{(1)}$moderately resistant strain, $^{(2)}$highly resistant strain; n.t. = not tested Compounds C22, C24, C25 and C30 have also been tested on various clinical isolates of rifampicin resistant strains of *S. aureus*, showing in the most of cases a MIC of from 0.125 to 2 µg/ml.

Compound C30 has further been tested against *Mycobacterium tuberculosis* and *Mycobacterium avium*, according to the following methodology:

*M. tuberculosis* was grown for 2–3 weeks on Lowenstein-Jensen medium (Sclavo) and *M. avium* on 7H10 agar (Difco) for 2 weeks. The cultures were suspended in 7H9 broth (Difco), diluted in Becton Dickinson diluting fluid, and inoculated into Bactec 12B vials (Becton Dickinson).

The inocula for control vials (without the compound to be tested) were $10^2$–$10^3$ cfu/ml; vials with compound C30 were inoculated with 100 times this number of cells. The vials were incubated at 37° C. and read daily in a Bactec 460 machine.

*M. tuberculosis* was considered sensitive to a given concentration of antibiotic if the difference between growth indexes on successive days in the vial was less than that of the control. *M. avium* was considered sensitive to a given antibiotic concentration if the growth index was less than that of the control.

The inhibitory concentration of compound C30 was found to be less than 0.2 against both the strains.

Some compounds of the invention were also tested in experimental septicemia in mice infected with *Staphylococcus aureus* Smith (Int. code L 819).

For this purpose, groups of five mice were infected intraperitoneally with about $1 \times 10^6$ CFU of *S. aureus* Smith suspended in 0.5 ml of Difco bacteriological mucin. Untreated animals died within 48 hours.

The other animals were treated once immediately after infection. On the 7th day the value of $ED_{50}$ (expressed in mg/kg) was calculated by the method of Spearman-Kärber (Finney, D. J., Statistical method in biological assay, page 254, C. Griffin Ltd., London, 1952), on the basis of the percentage of animals surviving at each dose.

The results are reported in the following table II:

TABLE II

Experimental septicemia in mice infected with *S. aureus* Smith (L 819)

| | $ED_{50}$ (mg/kg) | |
|---|---|---|
| Compound | SC route | IV route |
| C22 | 5.3 | 0.7 |
| C23 | 32.9 | n.t. |
| C24 | >50 | 3.8 |
| C25 | 4.7 | 2.9 |
| C26 | 1.6 | 0.95 |
| C30 | 1.6 | 0.72 |

SC = Subcutaneous; IV = Intravenous; n.t. = not tested

As shown in table II, when the compounds of the invention are administered by subcutaneous or intravenous routes, a good activity is observed in general. The activities of the above compounds were however negligible when administered orally.

In view of their properties, the compounds of the invention can be used as active ingredients in the preparation of medicaments for human or animal treatment.

In particular, the antibiotic compounds of general formula I are antimicrobial agents mainly active against gram positive bacteria, and fastidious gram negative bacteria.

Furthermore, the compounds of the invention show a considerable antimicrobial activity against those strain which have developed resistance to rifampicin.

The main therapeutic indication of the antibiotic substances of the invention is thus in the treatment of infections related to the presence of a microorganism susceptible to it.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compounds of the invention can be administered as such or in admixture with pharmaceutically acceptable carriers and can also be administered in conjunction with other antimicrobial agents generally employed in the art along with rifamycin antibiotics. Conjunctive therapy, thus includes sequential, simultaneous or separate administration of the active compound in a way that the therapeutical effects of the first administered one has not entirely disappeared when the subsequent one is administered.

The amount of active substance in the finished dosage form is related to a certain extent to the minimal inhibitory concentration of active substance against the infection causative agents and its particular type of formulation.

The dosage may obviously be adjusted according to the severity of the infection, the type, age and conditions of the patient, the formulation selected for the administration, the administration schedule, etc.

Experimental tests for determining the sensitivity of the microorganisms isolated from the patient may also offer useful indication to select the appropriate dosage.

In general, effective antimicrobial dosages are employed per single unit dosage form.

Repeated administrations, e.g. from 2 to 6 times a day, are in general preferred. An effective dosage may be in general in the range 0.5–100 mg/kg body weight/day, preferably 5–50 mg/kg body weight/day.

Anyway, the prescribing physician will be able to determine the optimal dosage for a given patient in a given situation.

The antibiotic compounds of the invention may be administered by parenteral (intramuscular, intravenous, subcutaneous, etc.) or oral route; the nature of the compound will determine the specific route of administration that may be employed. When the compound is not inactivated and is absorbed from the gastro-intestinal tract, the oral route is generally preferred; otherwise, and also in the case of the unconscious or uncooperative state of the patient, parenteral administration of the active substance may conveniently be employed.

For oral administration the compounds of the invention can be formulated into solid or liquid preparations such as capsules, pills, tablets, troches, powder, solutions, suspensions or emulsions.

For instance, the solid unit dosage form can be a capsule of the ordinary gelatin type containing lubricants and inert filler, such as lactose, sucrose and cornstarch. In another embodiment, the compounds of general formula I can be tableted with conventional tablet bases such as lactose, sucrose and cornstarch in combination with binders, such as acacia, cornstarch or gelatin, disintegrating agents such as potato starch or alginic acid and a lubricant such as stearic acid or magnesium stearate.

A unit dosage for oral administration may contain, for instance, from 50 to 700 mg of the active ingredient, preferably about 150 to 500 mg of the active ingredient.

For parenteral administration the compounds of the invention may be formulated into suitable injectable preparations containing a liquid vehicle. Such vehicle normally has no therapeutic effect and should not be toxic. Examples of suitable vehicles for preparing injectable dosage forms of the compounds of the invention are water, aqueous vehicles (e.g. Sodium chloride injections, Dextrose injections, etc.), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain buffers for stabilizing the solution (e.g. citrates, acetates and phosphates) and/or antioxidants (e.g. ascorbic acid or sodium bisulfite).

Also in the case of parenteral administration of the compounds of the invention, the nature of the product will determine the specific route of administration (e.g. intramuscular, intravenous or subcutaneous) that may be employed. Conversely, the desired route of administration will place requirements on the formulation. For example, suspensions would not be administered directly in the blood stream because of the danger of insoluble particles blocking capillaries, whilst solutions to be administered subcutaneously would require strict attention to tonicity adjustment, otherwise irritation of the nerve endings in the anatomical area would give rise to pronounced pain.

Useful indications for the preparations of suitable parenteral and oral dosage forms can be found in: Remington's Pharmaceutical Sciences, 17th Edition, 1985 (Mack Publishing Company, Easton, Pa.).

Besides their use as medicaments in human and veterinary therapy, the compounds of the invention may also be used as animal growth promoters.

For this purpose, a compound of the invention is administered orally in a suitable feed. The exact concentration employed will reflect the amount of active agent needed for a growth promotant effect and the amount of feed normally consumed.

The addition of the active compound of the invention to animal feed is preferably accomplished by preparing an appropriate feed premix containing the active compound in an efficacious amount and incorporating the premix into the complete ration. Alternatively, an intermediate concentrate or feed supplement containing the active ingredient can be blended into the feed.

The way in which such feed premixes and complete rations can be prepared and administered, are described in reference books (such as "Applied Animal Nutrition", W. H. Freedman and CO., S. Francisco, U.S.A, 1969 or "Livestock Feeds and Feeding", O and B books, Corvallis, Oreg., USA, 1977).

For better illustrate the present invention, examples of synthesis of compounds of general formula I are given hereinafter.

For the sake of clarity, the preparation of the starting material, of the intermediates and of the compounds of formula I has been so divided:

Preparations A to G refer to the preparation of the starting materials (the compounds obtained are marked with letter P, i.e. P1 to P7);

Examples A to I refer to the preparation of intermediate compounds (the compounds obtained are marked with letter E. i.e. E1 to E9);

Examples 1 to 30 refer to the preparation of the compounds of formula I, and also of those compounds wherein R is $(C_1-C_8)$alkyl (the compounds obtained are marked with letter C. i.e. C1 to C30).

In the following examples, the reaction is followed by means of TLC plates (silica-gel 60 $F_{254}$ pre-coated, 5×10 cm, thickness 0.25,Merck); the purification of the products obtained by flash-chromatography is performed on silica gel (32–63, 60 Å;

ICN Biomedicals GmbH), with methanol in dichloromethane as the eluent.

Preparation A: 25-O-Desacetyl-3-(4-morpholinyl)rifamycin S cyclic-21,23-(1-methylethylidene acetal) (Compound P1)

a) A mixture of rifamycin S (15 g), morpholine (40 ml) and dioxane (40 ml) is stirred 2 hours at room temperature. The mixture is cooled in icy water and 5N hydrochloric acid (45 ml) is added. Extraction with ethyl acetate (2×100 ml) and evaporation of the solvent give an oily residue which is dissolved in chloroform (100 ml) and stirred 2 hours with a 25% solution of potassium hexacyanoferrate (III) in water (100 ml). The organic phase is separated, washed with water, dried and evaporated to dryness. The residue is purified by flash-chromatography; elution with 2% methanol in dichloromethane gives pure 3-(4-morpholinyl) rifamycin S, of which, after crystallization from ethyl ether/ petroleum ether, 13.8 g are obtained; m.p. 180°–185° C. (dec). TLC (methanol:dichloromethane, 5:95): black spot, Rf 0.39.

b) Two drops of concentrated sulfuric acid are added to a mixture of 3-(4-morpholinyl) rifamycin S (11 g), 2,2-dimethoxypropane (11 ml) and dry acetone (120 ml). The reaction mixture is stirred 45 minutes at room temperature. Anhydrous sodium carbonate (1 g) is added and stirring continued for 5 min. The solution is filtered and evaporated to dryness. The residue is purified by flash-chromatography; elution with 1% methanol in dichloromethane affords 7.3 g of pure 3-(4-morpholinyl)rifamycin S cyclic-21,23-(1-methylethylidene acetal) which is dissolved in a cold solution of 5% NaOH in methanol (100 ml). The resulting mixture is stirred 18 hours at room temperature then diluted with icy water (100 ml), acidified (about pH 4) with citric acid and extracted with dichloromethane (3×100 ml). The combined extracts are dried and evaporated to dryness. The residue, by crystallization from ethyl ether/petroleum ether, gives the pure title compound (6.4 g) m.p. 171°–174° C. (dec). TLC (methanol:dichloromethane, 5:95): black spot, Rf 0.33. Analysis for $C_{42}H_{54}N_2O_{12}$, MW=778.904; Calculated C 64.76 H 6.99 N 3.59; Found C 64.57 H 7.01 N 3.39

Preparation B: 25-O-Desacetylrifamycin S cyclic-21,23-(1-methylethylidene acetal) (Compound P2)

The title compound is prepared as described by W. Kump and H. Birchel; Helv. Chim. Acta, 1973, 56, 2323.

Preparation C: 25-O-Deacetyl-2'-(diethylamino)rifamycin P cyclic-21,23-(1-methylethylidene acetal) (Compound P3)

N-Bromosuccinimide (2.2 g) in dimethylformamide (5 ml) is slowly dropped into a cold (5° C.) solution of Compound P2 (7.7 g) and triethylamine (1.25 g) in dimethylformamide (25 ml). The reaction mixture is stirred for 3 hours at room temperature, then 1,1-diethylthiourea (1.8 g) in dimethylformamide (4 ml) is added. Stirring is continued for 1.5 h, then ascorbic acid (2.6 g) in water (5 ml) is added. The mixture is allowed to rest overnight and then is poured into water (300 ml) and extracted with ethyl acetate (3×100 ml). The organic extracts are combined, washed with brine (200 ml), dried and evaporated to dryness. The residue is purified by flash-chromatography; elution with 1.8% methanol in dichloromethane gives the pure title compound (6.5 g).TLC (methanol:dichloromethane, 1:9): orange spot, Rf 0.54. Analysis for $C_{43}H_{57}N_3O_{10}S$, MW=808.031; Calculated C 63.92 H 7.11 N 5.20; Found C 63.59 H 7.26 N 5.06

Preparation D: 1-Ethyl-1,4-dihydro-6-(4-methyl-1-piperazinyl)-4-oxo-3-pyridinecarboxylic acid dihydrochloride (Compound P4)

a) ethyl 4,6-dichloronicotinate (17 g) is boiled for 4 hours with 24% sulfuric acid (400 ml). The white crystals that separate are filtered from the boiling solution and 4-chloro-6-hydroxynicotinic acid (6 g, m.p. 299°–300° C.) is obtained; the acidic solution is left overnight in the refrigerator. The crystallized solid is collected by filtration and dried under vacuum, thus obtaining 6-chloro-4-hydroxynicotinic acid (4.6 g) m.p. 231°–233° C.

b) A mixture of 6-chloro-4-hydroxynicotinic acid (4 g), absolute ethanol (120 ml), toluene (60 ml) and sulfuric acid (13 ml) is gently refluxed for 8 hours. After cooling the solvent is distilled off and the residue treated with icy water (100 ml). The solution is neutralized with a concentrated solution of $Na_2CO_3$ and then extracted with dichloromethane (3×100 ml). The combined extracts are dried over sodium sulfate and evaporated to dryness. The residue is dissolved in boiling ethyl ether (10 ml) then petroleum ether is added (10 ml); on cooling, ethyl 6-chloro-4-hydroxynicotinate (3.8 g) mp 59°–61° C.

c) A mixture of ethyl 6-chloro-4-hydroxynicotinate (3.7 g), powdered potassium carbonate (3.7 g), iodoethane (5 ml) and dimethylformamide (50 ml) is well stirred for 7 hours at 90° C. After cooling, the reaction mixture is filtered and the solvent evaporated off. The residue is treated with icy water (30 ml) and extracted with dichloromethane (2×30 ml). The combined extract are dried and evaporated to dryness. The residue is boiled 90 minutes with 1N sodium hydroxide (18 ml). After cooling the solution is extracted with diethyl ether (30 ml), that is discharged. The alkaline solution is concentrated to small volume, cooled and acidified to pH 4 with 1N hydrochloric acid. The white material that precipitates is collected and crystallized from ethanol to give 6-chloro-1,4-dihydro-1-ethyl-4-oxo-3-pyridine-carboxylic acid (3 g) m.p. 155°–57° C.

d) 6-chloro-1,4-dihydro-1-ethyl-4-oxo-3-pyridine-carboxylic acid (1.8 g) and N-methylpiperazine (5 ml) are stirred 5 hours at 130° C. The excess of amine is distilled off and the residue dissolved in 1M hydrochloric acid (10 ml). The acidic solution is evaporated to dryness and the residue crystallized from ethanol (4 ml). The alcoholic solution is kept overnight in the refrigerator, thus obtaining the title compound (1.1 g), m.p. 224°–226° C. Analysis for $C_{13}H_{19}N_3O_3.2HCl$ MW=338.236; Calculated N 12.42 Cl 20.96; Found N 11.97 Cl 20.80

Preparation E: 1-Cyclopropyl-7-(2,6-dimethyl-4-pyridinyl)-6-fluoro-1,4-dihydro-4-oxo-3-quinoline carboxylic acid (Compound P5)

a) Acetyl chloride (17 ml) is slowly dropped into a stirred mixture of 1-bromo-2,5-difluorobenzene (30 g) and aluminium trichloride (53 g) heated at 60° C. and kept under argon. The reaction mixture is then stirred 90 minutes at 95° C. The mixture is cooled at 40° C. and carefully poured into crushed ice (400 g) and concentrated hydrochloric acid (35 ml). The resulting mixture is stirred a few minutes and then extracted with ethyl ether (2×250 ml). The ethereal solution is washed to neutral with brine, dried over sodium sulfate and the solvent is evaporated. The distillation of the oily residue gives 4'-bromo-2',5'-difluoroacetophenone (21.2 g) b.p. (0.05 mm)=60° C.

b) Sodium hydride (7.1 g, 55% in mineral oil) is added in small portions to a well stirred solution of 4'-bromo-2',5'-difluoroacetophenone (20.8 g) in diethylcarbonate cooled at 5° C. The resulting mixture is stirred 10 minutes at 5° C. and 90 minutes at 80° C. After cooling the reaction mixture is poured into crushed ice (800 g) and acetic acid (35 ml), then extracted with ethyl ether (3×200 ml). The combined extracts are washed to neutral with brine dried over sodium sulfate and evaporated to dryness. The residue is purified by column chromatography containing 450 g of silica-gel (silica gel 60, particle size 0.063–0.200 mm Merck). Elution with 18% ethyl acetate in petroleum ether allows the separation of the less polar compound that, after crystallization from n-hexane gives ethyl 4-bromo-2,6-difluorobenzoylacetate (5.6 g) m.p. 49°–52° C.

c) Dimethylformamide dimethylacetal (2.4 ml) is slowly dropped into a stirred solution of ethyl 4-bromo-2,6-difluorobenzoylacetate (5.4 g) in dry tetrahydrofuran (15 ml). Stirring is continued overnight at room temperature, then the solvent is evaporated. The reddish oily residue is dissolved in dry tetrahydrofuran (22 ml) and cooled to 0° C.; cyclopropylamine (1.3 ml) is added and the resulting solution stirred 1 hour at 0° C. The solvent is evaporated under vacuum at room temperature. The residue, dissolved in dimethylformamide (25 ml), is stirred 1 hour at 100° C. with anhydrous potassium carbonate (4.5 g). After cooling the solution is filtered and evaporated to dryness. The residue is triturated with water, collected and recrystallized from ethanol to give ethyl 7-bromo-1-cyclopropyl-6-fluoro-1,4-dihydro-4-oxo-3-quinolinecarboxylate (3.2 g) 251°–253° C.

d) A mixture of 2,6-lutidine-N-oxide hydrochloride (48 g) and phosphorus oxychloride (110 ml) is heated 6.5 hours at reflux. After cooling the reaction mixture is carefully poured into crushed ice (1 kg). While the temperature is maintained below 15° C., concentrated ammonium hydroxide is added up to reach pH 8. The product that separates is extracted with ethyl ether (2×500 ml) which is dried and distilled off. The residue is dissolved in ethanol (400 ml) and boiled 3 hours with triethylamine (20 ml). After cooling, the solution is evaporated to dryness, treated with water (200 ml) and extracted with ethyl ether (4×150 ml). The combined extracts are dried and the solvent evaporated. The residue after distillation gives 4-chloro-2,6-dimethylpyridine (25 g), b.p. (15 mm)=67°–69° C. To a mixture of sodium (10 g, 30% dispersion in toluene) in anhydrous dimethoxyethane (40 ml) cooled in an ice-bath and kept under argon, trimethyltin chloride (12.1 g) in dimethoxymethane (6 ml) is added over a one hour period while keeping the temperature at 0° C. The mixture is stirred 2.5 hours at 0° C.; then 4-chloro-2,6-dimethylpyridine (7 g) in dimethoxyethane is slowly dropped into. Stirring is continued for an additional hour then the reaction mixture is allowed to stand overnight at room temperature. The reaction mixture is diluted with ethyl ether (100 ml) and filtered. The solvent is evaporated, the residue dissolved in ethyl ether (100 ml) and filtered again. After evaporation of the solvent the residue is distilled giving 2,6-dimethyl-4-(trimethyl-stannyl)pyridine (8.8 g), b.p. (15 m)=130°–140° C.

e) 2,6-dimethyl-4-(trimethylstannyl)pyridine (2.6 g) in dioxane (6 ml) is slowly dropped into a stirred mixture of ethyl 7-bromo-1-cyclopropyl-6-fluoro-1,4-dihydro-4-oxo-3-quinolinecarboxylate (3.1 g), dioxane (55 ml) and hexamethylenphosphoramide (2.6 ml) kept under argon. To the stirred mixture, dichlorobis (triphenylphosphine) palladium (0.4 g) is added. The reaction mixture is heated under reflux for 24 hours. After cooling it is poured in water (200 ml) and repeatedly extracted with dichloromethane. The organic extracts are dried and evaporated to dryness. The residue, after trituration with ethyl ether, gives ethyl 1-cyclopropyl-7-(2,6-dimethyl-4-pyridinyl)-6-fluoro-1,4-dihydro-4-oxo-3-quinolinecarboxylate (2.4 g) m.p. 196°–199° C.

f) A suspension of ethyl 1-cyclopropyl-7-(2,6-dimethyl-4-pyridinyl)-6-fluoro-1,4-dihydro-4-oxo-3-quinolinecarboxylate (2.3 g) in 1.5% NaOH (50 ml) is heated 2.5 h at reflux. The solution is decolorized with charcoal (1 g) filtered, cooled in an ice-bath and acidified with acetic acid. The separated solid is collected by filtration and crystallized from ethanol/chloroform to give the title compound (1.66 g) m.p. 300°–303° C.

Preparation F: Potassium salt of 1-ethyl-1,4-dihydro-6-(4-methyl-1-piperazinyl)-4-oxo-3-pyridinecarboxylic acid (Compound P6)

The potassium salt of compound P4 is prepared by adding 1N potassium hydroxide (6 ml) to the free acid dihydrochloride (676 mg–2 mmol) dissolved in water (5 ml). The aqueous solution is evaporated to dryness and the residue treated with boiling ethanol (20 ml). The insoluble material (KCl) is filtered and the alcoholic solution re-evaporated to dryness. The solid residue is triturated with diethyl ether, collected by filtration and dried over phosphorous pentoxide under vacuum giving the desired potassium salt (575 mg).

Preparation C: Potassium salt of 1–Cyclopropyl-7-(2,6-dimethyl-4-pyridinyl)-6-fluoro-1,4-dihydro-4-oxo-3-quinoline carboxylic acid (Compound P7)

The potassium salt of compound P5 is prepared by adding 1N potassium hydroxide (2 ml) to the free acid (705 mg–2mmol) dissolved in ethanol (10 ml). The resulting solution is evaporated to dryness and the solid residue is triturated with a 1:1 mixture of diethyl ether/ethanol, collected by filtration and dried over phosphorous pentoxide under vacuum giving the desired potassium salt (672 mg).

EXAMPLE A

36-Bromo-36-carboxyrifamycin S (Compound E1)

a) 1,3-Dicyclohexylcarbodiimide (950 mg, 4.6 mmol) dissolved in dry tetrahydrofuran (2 ml) is slowly dropped into a stirred mixture of compound P2 (940 mg, 1.4 mmol), bromomalonic acid (840 mg, 4.6 mmol) and dry tetrahydrofuran (15 ml) cooled at 0° C. The reaction mixture is stirred 15 minutes at 0° C., then 1 hour at room temperature. The dicyclohexylurea that forms is filtered off and the solution evaporated to dryness. The oily residue is dissolved in ethyl acetate (20 ml) and washed with water (2×20 ml). After drying over sodium sulfate, the solvent is evaporated and the residue purified by flash-chromatography. Elution with 4% methanol in dichloromethane gives pure (36-Bromo-36-carboxy)rifamycin S cyclic-21,23-(1-methylethylidene acetal) (680 mg). TLC (methanol:dichloromethane, 15:85): Rf 0.34 b) A mixture of the above obtained compound (680 mg), tetrahydrofuran (8 ml) and 3% sulfuric acid (3 ml) is stirred at 40° C. for 16 hours. After cooling, the reaction mixture is poured into water (20 ml) and extracted with ethyl acetate (2×20 ml). The organic extracts are washed with brine to neutral, then dried and concentrated to a small volume. Dilution with petroleum ether gives a brownish precipitate which is collected and dried under vacuum yielding the title compound (490 mg). TLC (methanol:dichloromethane, 15:85): Rf 0.27; Analysis for $C_{38}H_{44}BrN_{14}$, MW=818.682; Calculated C 55.75 H 5.41 N 1.85 Br 9.76; Found C 55.85 H 5.60 N 1.70 Br 8.98

EXAMPLE B

36-Carboxy-36-fluororifamycin S (Compound E2)

By following the procedure of Example A, but starting from Compound P2 (0.7 g) and fluoromalonic acid, the title compound is obtained (0.22 g). TLC (methanol:dichloromethane, 15:85): Rf 0.20; Analysis for $C_{38}H_{44}FNO_{14}$, MW=757.771; Calculated C 60.23 H 5.85 N 1.71; Found C 60.00 H 5.94 N 1.70

EXAMPLE C
36-Carboxy-36-chlororifamycin S (Compound E3)

By following the procedure of Example A, but starting from P2 (9.6 g) and chloromalonic acid, the title compound is obtained (9.3 g). TLC (methanol:dichloromethane, 2:8): Rf 0.45; Analysis for $C_{38}H_{44}ClNO_{14}$, MW=774.226; Calculated C 58.95 H 5.73 N 1.81 Cl 4.58; Found C 58.49 H 5.61 N 1.73 Cl 4.80

EXAMPLE D
36-Carboxy-36-methylthiorifamycin S (Compound E4)

By following the procedure of Example A, but starting from Compound P2 (0.96 g) and methylthiomalonic acid, the title compound is obtained (0.47 g). TLC (methanol:dichloromethane, 2:8): Rf 0.39; Analysis for $C_{39}H_{47}NO_{14}S$, MW=785.873; Calculated C 59.61 H 6.03 N 1.78 S 4.08; Found C 59.14 H 6.10 N 1.76 S 3.70

EXAMPLE E
36-Carboxy-36-ethylrifamycin S (Compound E5)

By following the procedure of Example A, but starting from Compound P2 (0.96 g) and ethylmalonic acid, the title compound is obtained (0.40 g). TLC (methanol:dichloromethane, 15:85): Rf 0.34; Analysis for $C_{40}H_{49}NO_{14}$, MW=767.836; Calculated C 61.01 H 6.43 N 1.82; Found C 60.58 H 6.50 N 1.79

EXAMPLE F
36-Carboxy-36-butylrifamycin S (Compound E6)

By following the procedure of Example A, but starting from Compound P2 (0.96 g) and butylmalonic acid, the title compound is obtained (0.4 g). TLC (methanol:dichloromethane, 1:9): Rf 0.51; Analysis for $C_{42}H_{53}NO_{14}$, MW=795.889 Calculated for C 63.38 H 6.71 N 1.76; Found C 62.96 H 6.75 N 1.70

EXAMPLE G
36-Carboxy-36-octylrifamycin S (Compound E7)

By following the procedure of Example A, but starting from Compound P2 (0.96 g) and octylmalonic acid, the title compound is obtained (0.66 g). TLC (methanol:dichloromethane, 1:9): Rf 0.55; Analysis for $C_{46}H_{61}NO_{14}$, MW=851.998; Calculated C 64.85 H 7.22 N 1.64; Found C 64.47 H 7.30 N 1.62

EXAMPLE H
36-Bromo-36-carboxy-3-(4-morpholinyl)-rifamycin S (Compound E8).

By following the procedure of Example A, but starting from Compound P1 (32 g) and bromomalonic acid, the title compound is obtained (26 g). TLC (methanol:dichloromethane, 2:8): Rf 0.43; Analysis for $C_{42}H_{51}BrN_2O_{15}$, MW=903.787; Calculated C 55.82 H 5.69 N 3.10 Br 8.84; Found C 55.30 H 5.70 H 3.04 Br 8.46

EXAMPLE I
36-Bromo-36-carboxy-2'-(diethylamino)-rifamycin P (Compound E9)

By following the procedure described in Example A, from Compound P3 (3.3 g) and bromomalonic acid (2.5 g), the title compound (1.4 g) is obtained. TLC (methanol:dichloromethane, 25:75): orange spot Rf 0.35; Analysis for $C_{43}H_{54}BrN_3O_{13}S$, MW=932.894; Calculated C 53.36 H 5.83 N 4.50 Br 8.61; Found C 54.01 H 5.93 N 4.61 Br 8.04

EXAMPLE 1
36-Bromorifamycin S (Compound C1)

Compound E1 (3.6 g) dissolved in anhydrous acetonitrile (40 ml) is very slowly added to a well stirred suspension of cuprous (I) oxide ($Cu_2O$) (100 mg) in anhydrous acetonitrile (160 ml) heated at 60° C. and kept under argon. The resulting mixture is stirred 1 hour at 60°–70° C. After cooling, it is filtered and evaporated to dryness. The residue, dissolved in ethyl acetate (40 ml), is washed with 1N hydrochloric acid (3×20 ml) and with brine to neutral. The organic phase is dried, the solvent evaporated off and the residue purified by flash-chromatography; elution with 1.2% methanol in dichloromethane allowed the isolation of the pure title compound (1.6 g). TLC (methanol:dichloromethane, 1:9): Rf 0.61; Analysis for $C_{37}H_{44}BrNO_{12}$, MW=774.673; Calculated C 57.36 H 5.73 N 1.80 Br 10.31; Found C 57.60 H 6.10 H 1.76 Br 10.24.

EXAMPLE 2
36-Fluororifamycin S (Compound C2)

By following the procedure of Example 1, but starting from Compound E2 (0.14 g) and $Cu_2O$ (0.01 g), the title compound is obtained (0.04 g). TLC (methanol:dichloromethane, 1:9): Rf 0.65; Analysis for $C_{37}H_{44}FNO_{12}$, MW=713.763; Calculated C 62.26 H 6.21 N 1.96; Found C 61.60 H 6.34 N 2.04

EXAMPLE 3
36-Chlororifamycin S (Compound C3)

By following the procedure of Example 1, but starting from Compound E3 (18.6 g) and $Cu_2O$ (0.48 g), the title compound is obtained (9.3 g). TLC (methanol:dichloromethane, 1:9): Rf 0.68; Analysis for $C_{37}H_{44}ClNO_{12}$, MW=730.217; Calculated C 60.86 H 6.07 N 1.92 Cl 4.85; Found C 61.00 H 6.30 N 1.76 Cl 4.73

EXAMPLE 4
36-Methylthiorifamycin S (Compound C4)

By following the procedure of Example A, but starting from Compound E4 (0.43 g) and $Cu_2O$ (0.03 g), the title compound is obtained (0.22 g). TLC (methanol:dichloromethane, 1:9): Rf 0.54; Analysis for $C_{38}H_{47}NO_{12}S$, MW=741.863; Calculated C 61.52 H 6.38 N 1.88 S 4.32; Found C 61.54 H 6.75 N 1.90 S 4.30

EXAMPLE 5
36-Ethylrifamycin S (Compound C5).

The procedure is essentially the same of Example 1 but the reaction mixture is stirred for 8 hours at the reflux. From 0.23 g of Compound E5 and 0.02 g of $Cu_2O$, the pure title compound is obtained (0.038 g). TLC (methanol:dichloromethane, 1:9): Rf 0.52; Analysis for $C_{39}H_{49}NO_{12}$, MW=723.726; Calculated C 64.72 H 6.82 N 1.93; Found C 63.98 H 6.90 N 2.13

EXAMPLE 6
36-Butylrifamycin S (Compound C6).

The procedure is as same as in Example 1 but the reaction mixture is stirred for 20 hours at reflux. From Compound E6 (0.40 g) and $Cu_2O$ (0.035 g), the title compound is obtained (0.030 g). TLC (methanol:dichloromethane, 1:9): Rf 0.7; Analysis for $C_{41}H_{53}NO_{12}$, MW=751.879; Calculated C 65.49 H 7.10 N 1.86; Found C 65.57 H 7.40 N 2.02

EXAMPLE 7
36-Octylrifamycin S (Compound C7).

By following the procedure of example 5, but starting from Compound E7 (0.65 g) and $Cu_2O$ (0.050 g), the title compound is obtained (0.150 g). TLC (methanol:dichloromethane, 1:9): Rf 0.75; Analysis for $C_{45}H_{61}NO_{12}$. MW=807.988; Calculated C 66.89 H 7.61 N 1.73; Found C 66.56 H 7.69 N 2.01

EXAMPLE 8
36-Bromo-3-(4-morpholinyl)rifamycin S (Compound C8)

By following the procedure of Example 1.but starting from Compound E8 (26 g) and $Cu_2O$ (0.70 g), the title compound is obtained (11.8 g). TLC (methanol:dichloromethane, 1:9): Rf 0.61; Analysis for $C_{41}H_{51}BrN_2O_3$. MW=859.777; Calculated C 57.27 H 5.99 N 3.26 Br 9.29; Found C 56.91 H 6.03 N 3.07 Br 8.81

EXAMPLE 9
36-Bromo-2'-(diethylamino)rifamycin P (Compound C9)

By following the procedure described in Example 1, from Compound E9 (1.6 g) and $Cu_2O$ (80 mg), the title compound (0.69 g) is obtained. TLC (methanol:dichloromethane, 1:9): orange spot Rf 0.5; Analysis for $C_{42}H_{54}BrN_3O_{11}S$, MW=888.884; Calculated C 56.75 H 6.12 N 4.72 Br 8.99; Found C 55.89 H 6.05 N 4.68 Br 9.30

EXAMPLE 10
36-Iodorifamycin S (Compound C10)

Sodium iodide (NaI) (0.47 g) dissolved in acetone (3 ml) is added to Compound C1 (1.12 g) dissolved in acetone (8 ml). The resulting mixture is stirred at room temperature for 4 hours. The solvent is evaporated off and the residue purified by flash-chromatogarphy. Elution with 1.4% methanol in dichloromethane gives pure title compound (1.1 g). TLC (methanol:dichloromethane, 1:9): Rf 0.59; Analysis for $C_{37}H_{44}INO_{12}$. MW=821.668; Calculated C 54.08 H 5.40 N 1.70; Found C 54.01 H 6.00 N 1.85

EXAMPLE 11
36-Iodo-3-(4-morpholinyl)rifamycin S (Compound C11)
By following the procedure of Example 10, but starting from compound Compound C8 (1.25 g) and NaI (0.5 g), the title compound is obtained (1.05 g). TLC (methanol:dichloromethane, 1:9): black spot Rf 0.6; Analysis for $C_{41}H_{51}IN_2O_{13}$. MW=906.772; Calculated C 54.31 H 5.67 N 3.09; Found C 53.82 H 5.75 N 2.79

EXAMPLE 12
36-Diethylaminorifamycin S (Compound C12)
A mixture of Compound C11 (300 mg), diethylamine (100 mg) and tetrahydrofuran (5 ml) is stirred 4 hours at room temperature, then poured into water (25 ml) and extracted with ethyl acetate (3×15 ml). The combined extracts are dried and evaporated to dryness. The residue is purified by flash-chromatography; elution with 2% methanol in dichloromethane gives the pure title compound (135 mg). TLC (methanol:dichloromethane, 1:9): Rf 0.5; Analysis for $C_{41}H_{54}N_2O_{12}$, MW=766.993; Calculated C 64.20 H 7.10 N 3.65; Found C 63.64 H 6.95 N 3.38

EXAMPLE 13
36-Acetyloxyrifamycin S (Compound C13)

A mixture of Compound C10 (180 mg), silver acetate (250 mg) and anhydrous dimethylformamide (18 ml) is stirred 18 hours at room temperature. The solvent is distilled off at 40° C. under vacuum. The residue is purified by flash-chromatography; elution with 1.2% methanol in dichloromethane allowed the recovery of unreacted Compound C10 (66 mg) as less polar component and the isolation of the pure title compound (41 mg). TLC (methanol:dichloromethane, 1:9): Rf 0.52; Analysis for $C_{39}H_{47}NO_{14}$. MW=753.809; Calculated C 62.14 H 6.28 N 1.86; Found C 61.48 H 6.40 N 1.85

EXAMPLE 14
36-Formyloxy-3-(4-morpholinyl)rifamycin S (Compound C14)

A mixture of potassium formate (11.5 g), dimethylformamide (800 ml) and activated 4 Åmolecular sieves (30 g) is stirred for 20 minutes. Compound C8 (11.5 g) is then added in small portions and stirring continued for 24 hours at room temperature. The mixture is filtered and the solvent removed at 40° C. under vacuum. The residue is purified by flash-chromatography; elution with 1.5% methanol in dichloromethane gives the pure title compound (8.6 g). TLC (methanol:dichloromethane, 1:9): black spot Rf 0.42; Analysis for $C_{42}H_{52}N_2O_{15}$. MW=824.886; Calculated C 61.15 H 6.35 N 3.40; Found C 60.41 H 6.37 N 3.30

EXAMPLE 15
36-Hydroxy-3-(4-morpholinyl)rifamycin S (Compound C15)

A solution of potassium bicarbonate (18 g) in water (180 ml) is slowly added to Compound C14 (8.2 g) dissolved in methanol (450 ml). The resulting mixture is stirred overnight at room temperature, then evaporated to dryness at 30° C. and under vacuum. Citric acid (10% W/V) is carefully added. The mixture is extracted with ethyl acetate (2×150 ml), which is then evaporated off. The residue is purified by flash-chromatography; elution with 1.8% methanol in dichloro-methane, after crystallization from ethyl ether, gives the pure title compound (4.3 g). M.P. 168°–171° C. (dec). TLC (methanol:dichloromethane, 5:95): black spot Rf 0.33; Analysis for $C_{41}H_{52}N_2O_{14}$. MW=796.876; Calculated C 61.79 H 6.58 N 3.51; Found C 61.30 H 6.56 N 3.22

EXAMPLE 16
36-Iodo-2'-diethylaminorifamycin P (Compound C16)

Sodium iodide (NaI) (0.2 g) dissolved in acetone (2 ml) is added to compound C9 (0.55 g) dissolved in acetone (4 ml). The resulting mixture is stirred at room temperature for 4 hours. The solvent is evaporated off and the residue purified by flash-chromatogarphy. Elution with 1.4% methanol in dichloromethane gives pure title compound (0.48 g). TLC (methanol:dichloromethane, 1:9): orange spot Rf 0.48; Analysis for $C_{42}H_{54}IN_3O_{11}S$. MW=953.879; Calculated C 53.90 H 5.82 N 4.49 S 3.42; Found C 54.04 H 5.82 N 4.48 S 3.21

EXAMPLE 17
36-Bromo-3-{[(4-methyl-1-piperazinyl)-imino]methyl}rifamycin SV (Compound C17)

a) N-methylen-t-butylamine (1.92 g) is slowly dropped into a cooled solution (15° C.) of Compound C1 (3.3 g) in tetrahydrofuran (25 ml). After an addition of tert-butylamine (0.4 ml), the reaction mixture is stirred for 5 minutes, then manganese dioxide (1.7 g) is added and stirring continued overnight at 48° C. After cooling, the mixture is filtered and dropped into a cold solution (0° C.) of 16% sulfuric acid (15 ml), ascorbic acid (3 g) and tetrahydrofuran (5 ml). The reaction mixture is stirred 3 hours at 45° C., then is poured in icy water (150 ml) and finally extracted with ethyl acetate (3×5 ml) that is dried and evaporated to dryness. The residue is purified by flash-chromatography; elution with 3% methanol in dichloromethane gives pure 36-Bromo-3-formylrifamycin SV (500 mg). TLC (methanol:dichloromethane, 85:15): red spot Rf 0.44; Analysis for $C_{38}H_{46}BrNO_{13}$. MW=804.699; Calculated for C 56.72 H 5.76 N 1.74 Br 9.93; Found C 56.06 H 5.94 N 2.00 Br 10.10 b) 1-Amino-4-methylpiperazine (50 mg) is added to the above obtained compound (300 mg) dissolved in tetrahydrofuran (7 ml). The solution is stirred 30 min at room temperature. The solvent is evaporated off and the residue dissolved in ethyl acetate; addition of petroleum ether leads to the precipitation of the pure title compound (280 mg). TLC (methanol:dichloromethane, 15:85): orange spot Rf 0.65; Analysis for $C_{43}H_{57}BrN_4O_{12}$, MW=901.862; Calculated C 57.27 H 6.37 N 6.21 Br 8.86; Found C 56.45 H 6.40 N 5.90 Br 8.34

EXAMPLE 18

36-Chloro-3{[(4-methyl-1-piperazinyl)-imino]methyl}rifamycin SV (Compound C18)

a) By following the procedure of Example 17, step a, but starting from Compound C3 (4.1 g), N-methylen-t-butylamine (2.6 g), tert-butylamine (0.5 ml) and manganese dioxide (2.3 g), 36-chloro-formylrifamycin SV is obtained (3.9 g). TLC (methanol:dichloromethane, 15:85): red spot Rf 0.47; Analysis for $C_{38}H_{46}ClNO_{13}$, MW=760.243; Calculated C 60.03 H 6.10 N 1.84 Cl 4.66; Found C 59.61 H 6.22 N 1.80 Cl 4.45 b) By following the procedure of Example 17, step b, but starting from the above obtained compound (3.9 g) and 1-Amino-4-methylpiperazine (0.67 g), the title compound (2.92 g) is obtained. TLC (methanol:dichloromethane, 15:85): orange spot Rf 0.61; Analysis for $C_{43}H_{57}ClN_4O_2$, MW=857.406; Calculated C 60.23 H 6.70 N 6.53 Cl 4.13; Found C 59.94 H 6.42 N 6.36 Cl 4.40

EXAMPLE 19

36-Iodo-3{[(4-methyl-1-piperazinyl)-imino]methyl}rifamycin SV (Compound C19)

Sodium iodide (110 mg) is added to Compound C17 (300 mg) dissolved in acetone (3 ml). The mixture is stirred 4 hours at room temperature and then evaporated to dryness. The residue is purified by flash-chromatography; elution with 3% methanol in dichloromethane gives pure title compound (160 mg).

Alternatively, Compound C18 (2.9 g) is reacted with sodium iodide (1 g) as above described, thus obtaining the pure title compound (2.83 g). TLC (methanol:dichloromethane, 15:85): orange spot Rf 0.63; Analysis for $C_{43}H_{57}IN_4O_{12}$, MW=948.857; Calculated C 54.43 H 6.05 N 5.90; Found C 54.70 H 6.20 N 5.49

EXAMPLE 20

36-Bromo-3{[(4-cyclopentyl-1-pipera-zinyl)imino]methyl}rifamycin SV (Compound C20)

a) By following the procedure of Example 17, step b, but starting from 36-Bromo-3-formylrifamycin SV (0.65 g) and 1-Amino-4-cyclopentylpiperazine (0.14 g), the title compound is obtained (0.64 g). TLC (methanol:dichloromethane, 15:85): orange spot Rf 0.64; Analysis for $C_{47}H_{63}BrN_4O_{12}$, MW=955.955; Calculated C 59.05 H 6.64 N 5.86 Br 8.36; Found C 58.38 H 6.39 N 5.60 Br 7.61

EXAMPLE 21

36-Iodo-3{[(4-cyclopentyl-1-pipera-zinyl)imino]methyl}rifamycin SV (Compound C21)

b) By following the procedure of Example 19, but starting from Compound C20 (730 mg) and sodium iodide (250 mg), the title compound (432 mg) is obtained.

EXAMPLE 22

36-[(1-Ethyl-6-fluoro-1,4-dihydro-7-(4-methyl-1-piperazinyl)-4-oxo-3-quinolinyl)carbonyloxy]-2'-(diethylamino)rifamycin P (Compound C22)

(1-Ethyl-6-fluoro-1,4-dihydro-7-(4-methyl-1-piperazinyl)-4-oxo-3-quinolinyl)carboxylic acid (Pefloxacin) potassium salt (440 mg) dissolved in dimethylformamide (44 ml) is stirred for 30 min with activated 4 Åmolecular sieves (Union Carbide type 4 Å, Fluka) (4.4 g). Compound C16 (440 mg) is added in small portions and stirring continued overnight at room temperature. The reaction mixture is filtered and evaporated to dryness at 40° C. under vacuum. The residue is purified by flash-chromatography; elution with 8% methanol in dichloromethane allows the isolation of the pure title compound (380 mg). TLC (methanol:dichloromethane, 1: 9): orange spot Rf 0.4; Analysis for $C_{59}H_{73}FN_6O_{14}S$, MW=1141.313; Calculated C 62.09 H 6.45 N 7.36 S 2.81; Found C 61.20 H 6.36 N 7.05 S 2.44

EXAMPLE 23

36-{2-[(1-Ethyl-6-fluoro-1,4-dihydro-7-(4-methyl-1-piperazinyl)-4-oxo-3-quinolinyl]carbonyloxy} rifamycin S (Compound C23)

Pefloxacin potassium salt (250 mg) is reacted with Compound C10 (250 mg) in dimethylformamide (25 ml) as described in Example 22. In this way the title compound (178 mg) is obtained. TLC (methanol:dichloromethane, 1:9): brown spot Rf 0.38; Analysis for $C_{54}H_{63}FN_4O_{15}$, MW=1027.120; Calculated C 63.14 H 6.18 N 5.45; Found C 62.50 H 5.98 N 5.06

EXAMPLE 24

36-{[1-Ethyl-6-fluoro-1,4-dihydro-7-(4-methyl-1-piperazinyl)-4-oxo-3-quinolinyl]carbonyloxy}-3-(4-morpholinyl) rifamycin S (Compound C24)

Compound C8 (460 mg) is reacted with Pefloxacin potassium salt (460 mg) in dimethylformamide (46 ml) as described in Example 22. The residue is purified by flash-chromatography; elution with 6% methanol in dichloromethane gives pure title compound (354 mg). TLC (methanol:dichloromethane, 1:9): black spot Rf 0.42; Analysis for $C_{58}H_{70}FN_5O_{16}$, MW=1112.225; Calculated C 62.63 H 6.34 N 6.29; Found C 61.72 H 6.37 N 5.95

EXAMPLE 25

36-{[1-Ethyl-6-fluoro-1,4-dihydro-7-(4-methyl-1-piperazinyl)-4-oxo-3-quinolinyl]carbonyloxy}-3-{[(4-methyl-1-piperazinyl)imino]methyl}rifamycin SV (Compound C25)

By reacting Pefloxacin potassium salt (650 mg) with Compound C19 (650 mg) in dimethylformamide (65 ml), as described in Example 22, the title compound (480 mg) is obtained after twice purification by flash-chromatography (eluition with increasing percentages—4 to 15%—of methanol in dichloromethane). TLC (methanol:dichloromethane, 2:8): orange spot Rf 0.47; Analysis for $C_{60}H_{76}FN_7O_{15}$, MW=1154.310; Calculated C 62.43 H 6.63 N 8.49; Found C 62.06 H 6.18 N 8.17

EXAMPLE 26

3{[(4-Cyclopentyl-1-piperazinyl)-imino]methyl}-36-{[1-ethyl-6-fluoro-1,4-dihydro-7-(4-methyl-1-piperazinyl)-4-oxo-3-quinolinyl]carbonyloxy}-rifamycin SV (Compound C26)

By following the procedure described in Example 25, but starting from the Compound C21 (400 mg) and Pefloxacin potassium salt (400 g), the title compound (280 mg) is obtained. TLC (methanol:dichloromethane, 2:8): orange spot Rf 0.60; Analysis for $C_{64}H_{82}FN_7O_{15}$, MW=1208.403; Calculated C 63.61 H 6.84 N 8.11; Found C 63.70 H 7.00 N 8.02

EXAMPLE 27

36-{[1-Ethyl-1,4-dihydro-7-methyl-4-oxo-1,8-naphthyridin-3-yl)carbonyloxy}-3{[(4-methyl-1-piperazinyl)imino]methyl}rifamycin SV (Compound C27)

According to the procedure of example 25, but starting from Compound C19 (500 mg) and [1-Ethyl-1,4-dihydro-7-methyl-4-oxo-1,8-naphthyridin-3-yl)carboxylic acid (Nalidixic Acid) potassium salt (500 mg), the title compound (452 mg) is obtained. TLC (methanol:dichloromethane, 1:9): red-orange spot Rf 0.49; Analysis for $C_{55}H_{68}N_6O_{15}$, MW=1053.186; Calculated C 62.72 H 6.51 N 7.98; Found C 61.86 H 6.43 N 7.79

EXAMPLE 28

36-{[8-Ethyl-5,8-dihydro-2-(4-methyl-1-piperazinyl)-5-oxopyrido[2,3-d]pyrimidin-6-yl]carbonyloxy}-3-{[(4-methyl-1-piperazinyl)imino]-methyl}rifamycin SV (Compound C28)

According to example 25, but starting from N-methyl-pipemidic acid potassium salt (400 mg) and Compound C19 (400 mg), the pure title compound (275 mg) is obtained. TLC (methanol:dichloromethane, 15:85): red-orange spot Rf 0.36; Analysis for $C_{58}H_{75}N_9O_{15}$, MW=1138.295; Calculated C 61.20 H 6.64 N 11.07; Found C 60.89 H 6.60 N 10.71

EXAMPLE 29

36-{[1-Cyclopropyl-6-fluoro-1,4-dihydro-7-(2,6-dimethyl-4-pyridinyl)-4-oxo-3-quinolinyl]-carbonyloxy}-3-{[(4-methyl-1-piperazinyl)imino]-methyl}rifamycin SV (Compound C29)

According to Example 25, but starting from Compound P7 (500 mg) and Compound C19 (500 mg), the pure title compound (420 mg) is obtained. TLC (methanol:dichloromethane, 1:9): red-orange spot Rf 0.45; Analysis for $C_{63}H_{73}FN_6O_{15}$, MW=1173.313; Calculated C 64.49 H 6.27 N 7.16; Found C 64.47 H 6.38 N 7.10

EXAMPLE 30

36-{[1-Ethyl-1,4-dihydro-6-(4-methyl-1-piperazinyl)-4-oxo-3-pyridinyl]carbonyloxy}-3-{[(4-methyl-1-piperazinyl)imino]methyl}rifamycin SV (Compound C30)

According to example 25, but starting from Compound P6 (500 mg) and Compound C19 (500 mg), the pure title compound (320 mg) is obtained. TLC (methanol:dichloromethane, 15:85): red-orange spot Rf 0.44; Analysis for $C_{56}H_{75}N_7O_{15}$, MW=1086.260; Calculated C 61.92 H 6.96 N 9.02; Found C 62.00 H 6.96 N 8.91;

We claim:
1. Compound of general formula I:

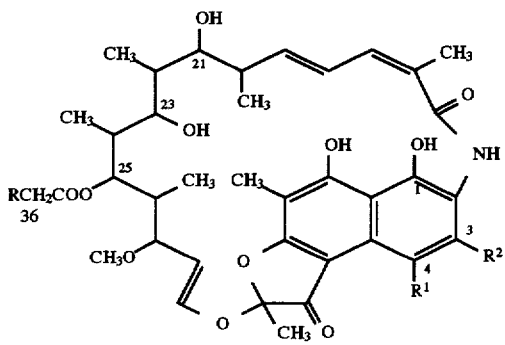

or the oxidated derivatives thereof of formula Ia:

wherein:
R represents, halo, hydroxy, thio, $(C_1-C_4)$alkoxy, $(C_1-C_4)$alkylthio, $(C_1-C_4)$acyloxy, $(C_1-C_4)$alkylamino, di$(C_1-C_4)$alkylamino or a group of formula:

wherein:
$R^3$ represents $(C_{1-4})$alkyl or $(C_3-C_6)$cycloalkyl;
$R^4$ represents a group of formula wherein:
$R^6$ and $R^7$ independently represent hydrogen or $(C_1-C_4)$ alkyl or
$R^6$ and $R^7$ together with the adjacent nitrogen atom form a five or six membered heterocyclic ring, optionally containing one further heteroatom selected from oxygen, nitrogen and sulfur, wherein one of the carbon or nitrogen atoms of the ring is optionally substituted by a $(C_1-C_4)$alkyl moiety;
$R^5$ is hydrogen or halogen;
or $R^4$ together with $R^5$ form a bifunctional alkylenic chain, optionally containing 1 or 2 nitrogen atoms, of the following formula:

wherein:
$R^8$ represents hydrogen or halogen;
$R^9$ represents $(C_1-C_4)$alkyl, or a six membered heterocycle ring containing one or two nitrogen atoms, wherein the carbon and nitrogen atoms of the ring are optionally substituted with one or two (C₁-C₄)alkyl moieties;

R¹ represents hydroxy in formula I or oxygen in formula Ia;

R² represents hydrogen, a five or six membered heterocyclic ring containing one or two heteroatoms selected from oxygen, nitrogen and sulfur, wherein one of the carbon or nitrogen atoms of the ring is optionally substituted by a (C₁-C₄)alkyl moiety, or a group of formula:

—CH=N—R¹⁰ wherein R¹⁰ represents a six membered heterocycle ring containing one or two nitrogen atoms, wherein one of the carbon or nitrogen atoms of the ring is optionally substituted by (C₁-C₄)alkyl or (C₅-C₆)cycloalkyl;

or R¹ and R² taken together form a group of formula =N—(CHR¹¹)—X—, —NH—(CHR¹¹)—X—, or —N=(CR¹¹)—X—, wherein:

X represents a sulfur atom or a —NH— group and R¹¹ represents hydrogen, (C₁-C₄)alkyl, (C₁-C₄)alkylamino or di(C₁-C₄)alkylamino;

and the pharmaceutically acceptale base addition salts thereof.

2. Compound according to claim 1 wherein:

R is halo, hydroxy, (C₁-C₄)acyloxy, (C₁-C₄)alkoxy, (C₁-C₄)alkylthio, di(C₁-C₄)alkylamino or a group of formula:

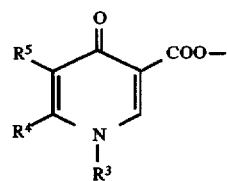

wherein:

R³ represents (C₁-C₄)alkyl or (C₃-C₆)cycloalkyl;

R⁴ represents a group of formula

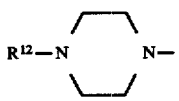

wherein R¹² represents hydrogen or (C₁-C₄)alkyl;

R⁵ is hydrogen or halo;

or R⁴ together with R⁵ form a bifunctional alkylenic chain, optionally containing 1 or 2 nitrogen atoms, of the following formula:

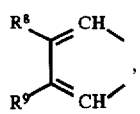 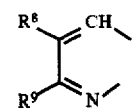 or 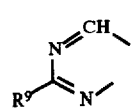

wherein R⁹ represents (C₁-C₄)alkyl, a group of formula

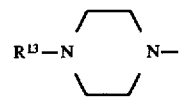

wherein R¹³ is hydrogen or (C₁-C₄)alkyl, or a group of formula

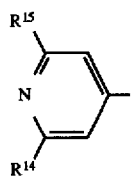

wherein R¹⁴ and R¹⁵ independently represent hydrogen or (C₁-C₄)alkyl;

R¹ is hydroxy in the reduced form or oxygen in the oxydated form;

R² represents hydrogen, a six membered heterocyclic ring containing one or two heteroatoms selected from oxygen, nitrogen and sulfur, wherein one of the carbon or nitrogen atoms of the ring is optionally substituted by a (C₁-C₄)alkyl moiety, or a group of formula:

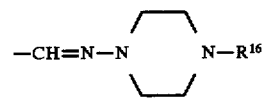

wherein R¹⁶ represents (C₁-C₄)alkyl or (C₅-C₆)cycloalkyl;

or R¹ and R² taken together form a group of formula —N=CR¹¹—S— wherein R¹¹ represents hydrogen, (C₁-C₄)alkyl or di(C₁-C₄)alkylamino.

3. Compound according to claim 1 wherein:

R is fluoro, bromo, chloro, iodo, hydroxy, formyl, acetyl, thiomethyl diethylamino or a group of formula:

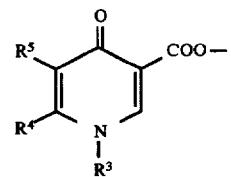

wherein:

R³ is ethyl or cyclopropyl, R⁴ is 4-methyl-1-piperazinyl and R⁵ is hydrogen;

or R⁴ together with R⁵ form a bifunctional alkylenic chain, optionally containing 1 or 2 nitrogen atoms, of formula:

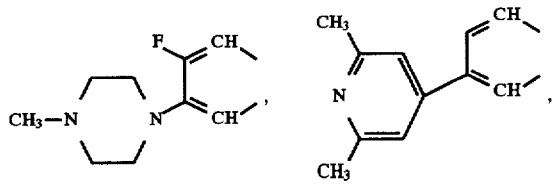

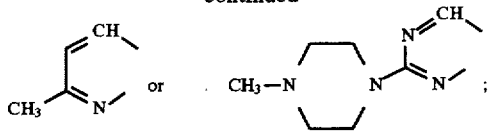

$R^1$ is hydroxy in the reduced form or oxygen in the oxydated form;

$R^2$ is hydrogen, 4-morpholinyl, {[(4-methyl-1-piperazinyl)imino]methyl} or {[(4-cyclopentyl-1-piperazinyl)imino]methyl};

or $R^1$ and $R^2$ together form a group of formula

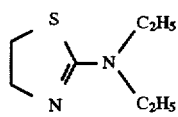

4. Compound according to claim 1 wherein:
R is bromo, chloro, iodo, hydroxy or a group of formula:

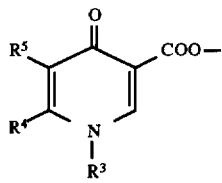

wherein:

$R^3$ is ethyl, $R^4$ is 4-methyl-1-piperazinyl and $R^5$ is hydrogen;

or $R^4$ together with $R^5$ form a bifunctional alkylenic chain of formula:

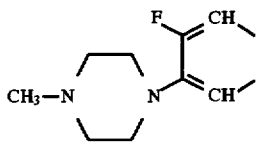

$R^1$ is hydroxy in the reduced form or oxygen in the oxydated form and $R^2$ is hydrogen, 4-morpholinyl or {[(4-methyl-1-piperazinyl)-imino]methyl}.

5. Compound according to claim 1, wherein the pharmaceutically acceptable salts of the compounds of formula I are formed with alkali metal, earth-alkali metal, $(C_1-C_4)$ alkylamines, $(C_1-C_4)$alkanolamines or basic aminoacids.

6. Compound according to claim 5 wherein the pharmaceutically acceptable salts are the sodium, arginine, lysine or histidine rifamycin salt.

7. Compound of general formula

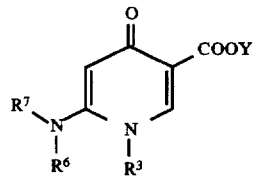

wherein:

Y represents hydrogen or $(C_1-C_4)$alkyl and $R^3$, $R^6$ and $R^7$ are as defined in claim 1, and the alkali metal salts thereof.

8. Process for preparing a compound of formula I wherein R is as defined in claim 1 with the further meaning of $(C_1-C_8)$alkyl, and $R^1$ and $R^2$ are as defined in claim 1, which comprises:

a) reacting a compound of general formula II

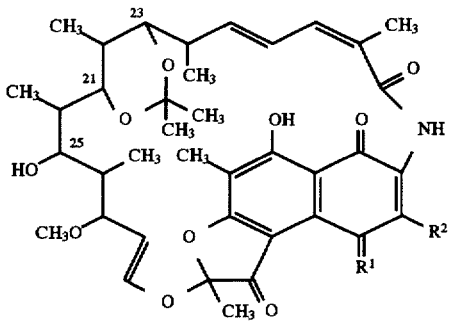

wherein $R^1$ and $R^2$ have the same meanings as in claim 1, with the proviso that $R^2$ is not a group of formula
—CH=N—$R^{10}$, with a malonic acid derivative of general formula III:

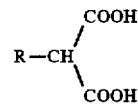

wherein R is as above defined, in the presence of a condensing agent and an inert organic solvent;

b) removing the protection in positions 21 and 23 by means of an acidic cleavage of the acetonidic moiety in the presence of an inert organic solvent; and c) contacting the obtained deprotected intermediate compound with a cuprous salt or oxide or a mixture thereof in the presence of an inert organic solvent.

9. Process according to claim 8 wherein the inert organic solvents of steps a, b and c are selected from alkylamides, alkylnitriles, saturated linear or cyclic ethers, glycol ethers, phosphoramides, sulfoxides, chlorinated solvents and mixtures thereof.

10. Process according to claim 8 wherein the inert organic solvent of step a and b is tetrahydrofuran and the inert organic solvent of step c is acetonitrile.

11. Process according to claim 8 wherein the condensing agent of step a is selected from carboxydiimides, dialkylaminopyridines, carbonylimidazoles, triphenilphosphine, substituted dithiocarbonates and diphenylphosphorilazides.

12. Process according to claim 8 wherein the condensing agent of step a is 1,3-Dicyclohexyl-carbodiimmide.

13. Process according to claim 8 wherein the acidic cleavage of the acetodinic moiety is performed by means of a mineral acid or an organic sulfonic acid.

14. Process according to claim 8 wherein the acidic cleavage of the acetodinic moiety is performed by means of sulfuric acid.

15. Process according to claim 8 wherein the decarboxylating agent of step c is selected from $Cu_2O$, $Cu_2S$, CuCl, CuBr and $Cu_2SO_4$ or a mixture thereof.

16. Process according to claim 8 wherein the decarboxylating agent of step c is cuprous oxide.

17. Process according to anyone of the claims from 8 wherein the reaction temperature of step a is from 0° C. to 35° C, the reaction, the reaction temperature of step b is from 30° C. to 50° C. and the reaction temperature of step c is conducted at temperature from 50° C. to 75° C.

18. Process for preparing a compound of general formula I, wherein R is as defined in claim 1, $R^1$ is oxygen and $R^2$ is a group —CH=N—$R^{10}$, wherein $R^{10}$ is as defined in claim 1, which comprises contacting a compound of general formula I, wherein R and $R^1$ are as above defined and $R^2$ is hydrogen with N-methylene-t-butylamine in the presence of t-butylamine and manganese dioxide and then with a compound of formula $NH_2$-$R^{10}$, wherein $R^{10}$ is as above defined.

19. Process for preparing a compound of general formula I, wherein R is iodo and $R^1$ and $R^2$ are as defined, which comprises contacting a compound of general formula I, wherein R is chloro or bromo and $R^1$ and $R^2$ are as defined, with an acetone solution of an alkali metal iodide.

20. Process for preparing a compound of general formula I, wherein R is ($C_1$–$C_4$)acyloxy and $R^1$ and $R^2$ are as defined, which comprises reacting a compound of general formula I, wherein R is chloro, bromo or iodo and $R^1$ and $R^2$ are as defined, with a ($C_1$–$C_4$)acylate salt, in the presence of an inert organic solvent.

21. Process for preparing a compound of general formula I, wherein R is ($C_1$–$C_4$)alkylamino or ($C_1$–$C_4$)dialkylamino and $R^1$ and $R^2$ are as defined, which comprises reacting a compound of general formula I, wherein R is chloro, bromo or iodo and $R^1$ and $R^2$ are as defined, with a mono- or di($C_1$–$C_4$)alkylamine, in the presence of an inert organic solvent.

22. Process for preparing a compound of general formula I, wherein R is hydroxy and $R^1$ and $R^2$ are as defined, which comprises hydrolizing a compound of general formula I, wherein R is formyloxy and $R^1$ and $R^2$ are as defined, under mild basic conditions in an hydroalcoholic solution.

23. Process for preparing a compound of general formula I, wherein R is a group of formula

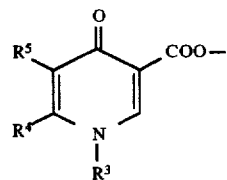

as defined in claim 1 and $R^1$ and $R^2$ are as defined in claim 1, which comprises reacting a compound of general formula I, wherein R is chloro, bromo or iodo and $R^1$ and $R^2$ are as defined, with a salt of a 4-oxo-3-pyridinyl carboxylic acid derivative of general formula IV

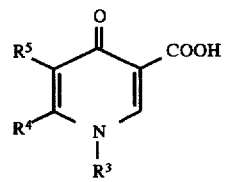

IV wherein $R^3$, $R^4$ and $R^5$ are as above defined, in the presence of an inert organic solvent.

24. Process according to claim 23 wherein the potassium salt of the 4-oxo-3-pyridinyl carboxylic acid derivative is employed.

25. Pharmaceutical composition containing as an active ingredient a compound of claim 1, in admixture with a pharmaceutically acceptable carrier.

26. Method of treatment of infections related to the presence of microorganisms susceptible to a compound of claim 1 which comprises administering an effective amount of a compound of claim 1 to a patient in need thereof.

* * * * *